United States Patent

Corti et al.

(10) Patent No.: US 12,285,465 B2
(45) Date of Patent: Apr. 29, 2025

(54) COMBINED TREATMENT OF PRIMARY CENTRAL NERVOUS SYSTEM LYMPHOMA

(71) Applicant: FONDAZIONE CENTRO SAN RAFFAELE, Milan (IT)

(72) Inventors: Angelo Corti, Milan (IT); Andrés José Maria Ferreri, Milan (IT)

(73) Assignee: FONDAZIONE CENTRO SAN RAFFAELE, Milan (IT)

(*) Notice: Subject to any disclaimer, the term of this patent is extended or adjusted under 35 U.S.C. 154(b) by 841 days.

(21) Appl. No.: 17/297,794

(22) PCT Filed: Dec. 2, 2019

(86) PCT No.: PCT/EP2019/083322
§ 371 (c)(1),
(2) Date: May 27, 2021

(87) PCT Pub. No.: WO2020/109625
PCT Pub. Date: Jun. 4, 2020

(65) Prior Publication Data
US 2022/0008513 A1  Jan. 13, 2022

Related U.S. Application Data

(60) Provisional application No. 62/773,473, filed on Nov. 30, 2018.

(51) Int. Cl.
| | |
|---|---|
| *A61K 38/19* | (2006.01) |
| *A61K 31/475* | (2006.01) |
| *A61K 31/573* | (2006.01) |
| *A61K 31/675* | (2006.01) |
| *A61K 31/704* | (2006.01) |
| *A61K 39/00* | (2006.01) |
| *A61K 39/395* | (2006.01) |
| *A61P 35/00* | (2006.01) |

(52) U.S. Cl.
CPC .......... *A61K 38/191* (2013.01); *A61K 31/475* (2013.01); *A61K 31/573* (2013.01); *A61K 31/675* (2013.01); *A61K 31/704* (2013.01); *A61K 39/3955* (2013.01); *A61P 35/00* (2018.01); *A61K 2039/505* (2013.01); *A61K 2039/545* (2013.01)

(58) Field of Classification Search
CPC .. A61K 38/191; A61K 31/475; A61K 31/573; A61K 31/675; A61K 31/704
See application file for complete search history.

(56) References Cited

U.S. PATENT DOCUMENTS

2015/0246123 A1  9/2015 Doshi

FOREIGN PATENT DOCUMENTS

| AU | 2008207357 A1 | 9/2008 |
| EP | 2364995 A1 | 9/2011 |
| WO | 01/061017 A2 | 8/2001 |
| WO | 2004/041297 A2 | 5/2004 |

OTHER PUBLICATIONS

Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Bork. Powers and Pitfalls in Sequence Analysis: The 70% Hurdle. Genome Research, 2000, 10:398-400 (Year: 2000).*
Greenspan et al. 1999. Defining epitopes: It's not as easy as it seems; Nature Biotechnology, 17:936-937 (Year: 1990).*
Ferreri. RCHOP Chemoimmunotherapy Preceded by BBB Permeabilization by t-NGR Necrosis Factor (Ingrid). Available from: https://clinicaltrials.gov/study/NCT03536039?term=nct03536039&rank=1&tab=history&a=1. NLM identifier. NCT03536039. First posted May 24, 2018 (Year: 2018).*
Ferreri et al. R-CHOP Preceded by Engineered Tumor Necrosis Factor (TNF) in Patients with Relapsed or Refractory (r/r) Primary CNS Lymphoma (PCNSL): Results of Antitumor Activity, Safety and Blood-Brain Barrier (BBB) Permeabilization in the "Ingrid" Phase II. Blood, 2018, 132 (supplement 1):1687 (Year: 2018).*
Coiffier et al. CHOP Chemotherapy plus Rituximab Compared with CHOP Alone in Elderly Patients with Diffuse Large-B-Cell Lymphoma. N Engl J Med 2002; 346:235-242 (Year: 2002).*
Curnis et al. Improving chemotherapeutic drug penetration in tumors by vascular targeting and barrier alteration. J Clin Invest. 2002; 110(4):475-482. (Year: 2002).*
Coiffier et al. N Engl J Med 2002; 346:235-242. (Year: 2002).*
Ferreri, Andres J M; et al, "R-CHOP Preceded by Engineered Tumor Necrosis Factor (TNF) in Patients with Relapsed or Refractory (r/r) Primary CNS Lymphoma (PCNSL): Results of Antitumor Activity, Safety and Blood-Brain Barrier (BBB) Permeabilization in the "Ingrid" Phase II Trial", Blood, vol. 132, No. Suppl. 1, Nov. 29, 2018 (Nov. 29, 2018), p. 1687 Abstract only.

(Continued)

*Primary Examiner* — Vanessa L. Ford
*Assistant Examiner* — Sandra Carter
(74) *Attorney, Agent, or Firm* — Lucas & Mercanti, LLP

(57) ABSTRACT

The present invention refers to the combination of an R-CHOP therapy with an administration of NGR-hTNF or an analog thereof for the treatment of primary central nervous system lymphoma, preferably relapsed/refractory primary central nervous system lymphoma.

Figure 1:
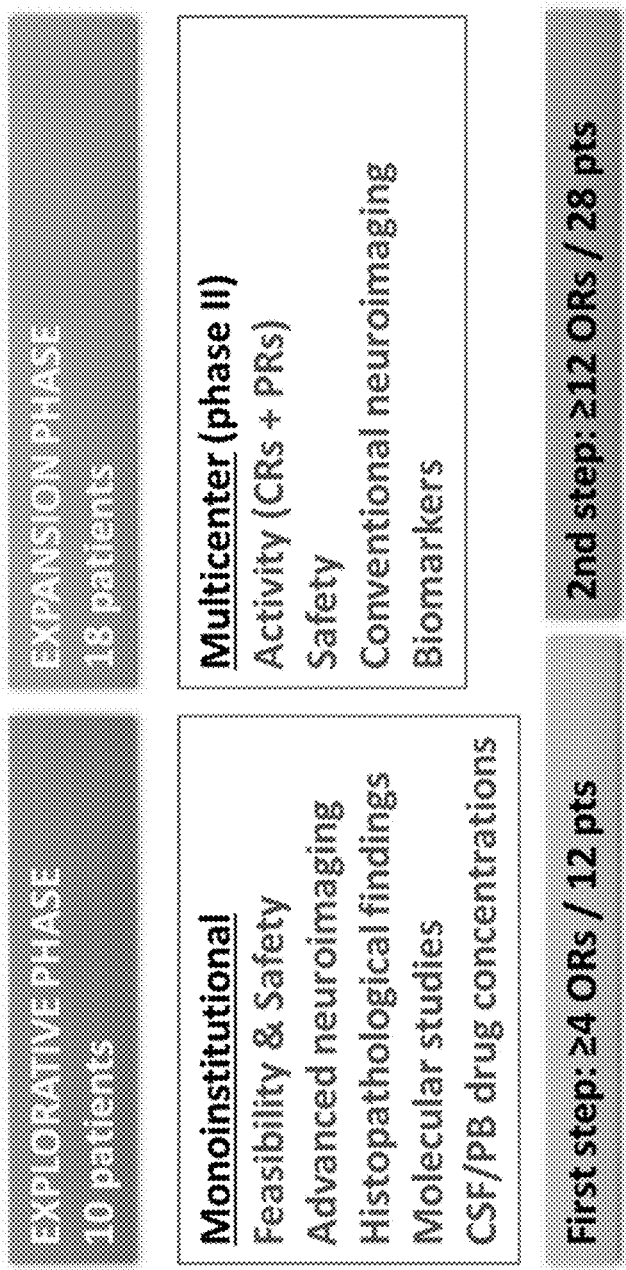

7 Claims, 10 Drawing Sheets
Specification includes a Sequence Listing.

(56) References Cited

OTHER PUBLICATIONS

ISR/EP, "PCT International Search Report and Written Opinion", issued in connection with PCT International Application No. PCT/EP2019/083322, which was mailed Mar. 30, 2020 (17 pages).

* cited by examiner

SEQUENCE LISTING

<160> NUMBER OF SEQ ID NOS: 7

<210> SEQ ID NO 1
<211> LENGTH: 165
<212> TYPE: PRT
<213> ORGANISM: Homo sapiens

<400> SEQUENCE: 1

Cys Asn Gly Arg Cys Gly Val Arg Ser Ser Arg Thr Leu Ser Asp
1               5                   10                  15

Lys Pro Val Ala His Val Val Ala Asn Pro Gln Ala Glu Gly Gln Leu
            20                  25                  30

Gln Trp Leu Asn Arg Arg Ala Asn Ala Leu Leu Ala Asn Gly Val Glu
            35                  40                  45

Leu Arg Asp Asn Gln Leu Val Val Pro Ser Glu Gly Leu Tyr Leu Ile
        50                  55                  60

Tyr Ser Gln Val Leu Phe Lys Gly Gln Gly Cys Pro Ser Thr His Val
65                  70                  75                  80

Leu Leu Thr His Thr Ile Ser Arg Ile Ala Val Ser Tyr Gln Thr Lys
                85                  90                  95

Val Asn Leu Leu Ser Ala Ile Lys Ser Pro Cys Gln Arg Glu Thr Pro
            100                 105                 110

Glu Gly Ala Glu Ala Lys Pro Trp Tyr Glu Pro Ile Tyr Leu Gly Gly
            115                 120                 125

Val Phe Gln Leu Glu Lys Gly Asp Arg Leu Ser Ala Glu Ile Asn Arg
        130                 135                 140

Pro Asp Tyr Leu Asp Phe Ala Glu Ser Gly Gln Val Tyr Phe Gly Ile
145                 150                 155                 160

Ile Ala Leu His Met
                165

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide

<400> SEQUENCE: 2

Cys Asn Gly Arg Cys Val Ser Gly Cys Ala Gly Arg Cys
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Asn Gly Arg Ala His Ala
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

```
Gly Asn Gly Arg Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic cyclic peptide

<400> SEQUENCE: 5

Cys Val Leu Asn Gly Arg Met Glu Cys
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic cyclic peptide

<400> SEQUENCE: 6

Cys Asn Gly Arg Cys
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Cys Asn Gly Arg Cys
1               5
```

COMBINED TREATMENT OF PRIMARY CENTRAL NERVOUS SYSTEM LYMPHOMA

CROSS-REFERENCE TO RELATED APPLICATIONS

This application is a 371 of PCT/EP2019/083322, filed Dec. 2, 2019, which claims the benefit of U.S. Provisional Application No. 62/773,473, filed Nov. 30, 2018.

REFERENCE TO A SEQUENCE LISTING SUBMITTED ELECTRONICALLY VIA EFS-WEB

The content of the electronically submitted sequence listing, file name: 128-1203-W-US_seq_ST25.txt; size: 2,896 bytes; and date of creation: Aug. 15, 2024, is incorporated herein by reference in its entirety.

TECHNICAL FIELD

The present invention refers to the combination of a R-CHOP therapy with an administration of NGR-hTNF or an analog thereof for the treatment of primary central nervous system lymphoma.

BACKGROUND ART

Primary diffuse large B-cell lymphoma of the CNS (PCNSL) is an aggressive malignancy with the peculiar clinical behavior to remain confined to the CNS, with rare cases of extra-CNS dissemination[1]. In comparison with limited-stage extra-CNS DLBCL, PCNSL patients show poorer survival figures, which has been attributed, at least in part, to the inefficacy of drugs currently used to treat extra-CNS DLBCL (i.e., R-CHOP regimen: rituximab, cyclophosphamide, doxorubicin, vincristine, and prednisone) to cross the blood-brain barrier (BBB) and achieve good CNS bioavailability[2]. Currently, PCNSL patients are treated with high-dose methotrexate-based combinations, often in association with cytarabine, alkylating agents and rituximab[3]. The diffuse use of these modern combinations has significantly improved survival in PCNSL patients, but these treatments require hospitalization, adequate direct experience and are burdened by relevant toxicity[4]. Conversely, enhanced CNS delivery of R-CHOP drugs could have the advantage of a well-tolerated therapy that does not require hospitalization and is widely used in onco-haematological centers. Therefore, the use of intravenous agents able to induce a reversible BBB permeabilization to enhance CNS cytostatics bioavailability is an attractive investigational approach in PCNSL patients.

Intravenous delivery of tumor necrosis factor (TNF) is followed by selective BBB permeabilization and enhances tumor penetration of chemotherapeutic agents in animal models of brain metastasis[6]. TNF is an inflammatory cytokine with potent anti-tumor activity, but its use in cancer patients is limited by prohibitive systemic toxicity[7]. A growing body of evidence suggests that the therapeutic index of this cytokine can be enhanced by a vascular targeting approach[8]. This can be achieved, for example, by fusing the N-terminus of human TNF with CNGRCG, a tumor vasculature-homing peptide capable of recognizing a isoform of aminopeptidase N (CD13), a membrane-bound metalloproteinase up-regulated in angiogenic tumor blood vessels[9,10] and barely or not at all expressed by normal blood vessels[11]. The CNGRCG-TNF fusion protein made with human TNF (developed at the San Raffaele Scientific Institute of Milan, Italy, and called NGR-hTNF) allows the delivery of extremely low, yet pharmacologically active, doses of cytokine to the tumor vasculature, thereby avoiding systemic toxic reaction and counter-regulatory mechanisms[12]. Studies performed in melanoma and lymphoma animal models have shown that low-dose NGR-hTNF can locally enhance vascular permeability and increase the penetration of chemotherapeutic drugs in tumor tissues[8,10,12,14].

Based on these notions, we hypothesized that low-dose NGR-hTNF can alter the BBB and enhance the penetration and activity of R-CHOP in patients with PCNSL. As a part of a translational research program of NGR-hTNF, we designed a prospective phase II trial aimed to assess the feasibility and activity of 6 courses of R-CHOP chemoimmunotherapy preceded by BBB permeabilization with low intravenous doses of NGR-hTNF in patients with relapsed or refractory PCNSL. In a per-protocol planned "proof-of-principle" part of the trial, changes in the BBB permeability in the lymphomatous lesions and in the normal-appearing brain parenchyma were investigated by Dynamic Contrast Enhanced (DCE) Magnetic Resonance Imaging (MRI) and single photon emission computed tomography (SPECT) in the first ten enrolled patients.

Changes in the concentrations of R-CHOP drugs in plasma and cerebrospinal fluid (CSF) samples and expression of CD13, the target of NGR-hTNF, in diagnostic biopsies were investigated as indicators of the specificity of the effect of NGR-hTNF on tumor vasculature. Herein, we report the results of this "proof-of-principle" study as the first step forward the development of a simple, manageable and active treatment for PCNSL patients, analogous to the worldwide used treatment of extra-CNS DLBCL.

SUMMARY OF THE INVENTION

Diffuse large B-cell lymphoma (DLBCL) is treated with R-CHOP (rituximab, cyclophosphamide, doxorubicin, vincristine, prednisone) with acceptable tolerability and efficacy. However, this chemoimmunotherapy is inefficacious in primary DLBCL of the CNS (PCNSL) because of its poor penetration of the blood-brain barrier. Tumor Necrosis Factor-α coupled with NGR (NGR-hTNF), a peptide targeting CD13+ tumor vessels, induces endothelial permeabilization and drug penetration in lymphoma-bearing mice. In the present invention the safety, activity and vascular permeability changes of R-CHOP21 preceded by NGR-hTNF in patients with relapsed/refractory PCNSL within a phase-II trial was addressed. NGR-hTNF/R-CHOP combination was well tolerated. Dynamic contrast-enhanced MRI and $^{99m}$Tc-DTPA SPECT demonstrated that NGR-hTNF selectively increased vascular permeability in tumoral/peritumoral areas, where CD13 was invariably expressed. NGR-hTNF did not influence plasma/CSF concentrations of R-CHOP drugs. Neuroimaging, histopathological and pharmacokinetic results were consistent with activity of NGR-hTNF/R-CHOP, which was associated with fast and prominent tumor regression in 7/10 patients.

In the present invention it was surprisingly found that R-CHOP administration preceded by low-dose NGR-hTNF is a safe and active approach, with fast and prominent tumor regression in 7/10 PCNSL patients. This innovative strategy represents a first-line treatment.

Therefore, the present invention provides a combination of R-CHOP (rituximab, cyclophosphamide, doxorubicin, vincristine and prednisone) and NGR-hTNF or an analog thereof for use in the treatment of primary central nervous system lymphoma in a subject, wherein the combination comprises at least one course of R-CHOP preceded by an administration of NGR-hTNF or an analog thereof.

NGR-hTNF analogs are described in WO 2004/041297 and WO 01/61017 incorporated by reference.

Preferably a course of R-CHOP consists of 375 mg/m² of rituximab, 750 mg/m² of cyclophosphamide, 50 mg/m² of doxorubicin and 1.4 mg/m² of vincristine.

Preferably a course of R-CHOP consists of 375 mg/m² of rituximab in day 1, 750 mg/m² of cyclophosphamide, 50 mg/m² of doxorubicin and 1.4 mg/m² of vincristine in day 2. Preferably the administration of NGR-hTNF or of an analog thereof is performed before CHOP drugs.

Preferably, the NGR-hTNF administration consists of 0.8 ug/m².

In a preferred embodiment the combination comprises six courses of R-CHOP each preceded by an administration of NGR-hTNF or an analog thereof.

Preferably, the courses of R-CHOP preceded by an administration of NGR-hTNF or an analog thereof are separated by 18 to 21 days.

The treated tumor is preferably a primary central nervous system lymphoma that relapsed or is refractory.

By relapsed or refractory it is meant a tumor that relapses or is resistant to standard upfront care. Such upfront care is for instance a high-dose-methotrexate-based chemotherapy, with or without rituximab. A primary central nervous system lymphoma that relapsed or is refractory means that the lymphoma relapsed after or is refractory to standard first-line treatment (for instance high-dose-methotrexate-based chemotherapy, with or without rituximab). First-line treatment is any known treatment known to the skilled person in the art.

The term "relapsed" refers to disease that reappears or grows again after a period of remission. The term "refractory" is used to describe when the lymphoma does not respond to treatment (meaning that the cancer cells continue to grow) or when the response to treatment does not last very long.

The term "peptide" as used herein includes polypeptides and proteins. The term "polypeptide" includes single-chain polypeptide molecules as well as multiple-polypeptide complexes where individual constituent polypeptides are linked by covalent or non-covalent means. The term "polypeptide" includes peptides of two or more amino acids in length, typically having more than 5, 10 or 20 amino acids.

It will be understood that polypeptide sequences for use in the invention are not limited to the particular sequences or fragments thereof but also include homologous sequences obtained from any source, for example related viral/bacterial proteins, cellular homologues and synthetic peptides, as well as variants or derivatives thereof. Polypeptide sequences of the present invention also include polypeptides encoded by polynucleotides of the present invention.

The terms "variant" or "derivative" in relation to the amino acid sequences of the present invention includes any substitution of, variation of, modification of, replacement of, deletion of or addition of one (or more) amino acids from or to the sequence providing the resultant amino acid sequence preferably has targeting activity, preferably having at least 25 to 50% of the activity as the polypeptides presented in the sequence listings, more preferably at least substantially the same activity.

Thus, sequences may be modified for use in the present invention. Typically, modifications are made that maintain the activity of the sequence.

Thus, in one embodiment, amino acid substitutions may be made, for example from 1, 2 or 3 to 10, 20 or 30 substitutions provided that the modified sequence retains at least about 25 to 50% of, or substantially the same activity. However, in an alternative embodiment, modifications to the amino acid sequences of a polypeptide of the invention may be made intentionally to reduce the biological activity of the polypeptide. For example, truncated polypeptides that remain capable of binding to target molecule but lack functional effector domains may be useful.

In general, preferably less than 20%, 10% or 5% of the amino acid residues of a variant or derivative are altered as compared with the corresponding region depicted in the sequence listings.

Amino acid substitutions may include the use of non-naturally occurring analogues, for example to increase blood plasma half-life of a therapeutically administered polypeptide (see below for further details on the production of peptide derivatives for use in therapy). Conservative substitutions may be made, for example according to the Table below. Amino acids in the same block in the second column and preferably in the same line in the third column may be substituted for each other:

| ALIPHATIC | Non-polar | G A P |
|           |           | I L V |
|           | Polar - uncharged | C S T M |
|           |           | N Q |
|           | Polar - charged | D E |
|           |           | K R |
| AROMATIC  |           | H F W Y |

Polypeptides of the invention also include fragments of the above mentioned polypeptides and variants thereof, including fragments of the sequences. Preferred fragments include those which include an epitope or binding domain. Suitable fragments will be at least about 5, e. g. 10, 12, 15 or 20 amino acids in length. They may also be less than 200, 100 or 50 amino acids in length. Polypeptide fragments of the proteins and allelic and species variants thereof may contain one or more (e. g. 2, 3, 5, or 10) substitutions, deletions or insertions, including conserved substitutions. Where substitutions, deletion and/or insertions have been made, for example by means of recombinant technology, preferably less than 20%, 10% or 5% of the amino acid residues depicted in the sequence listings are altered.

Polypeptides and conjugates of the invention are typically made by recombinant means, for example as described below. However, they may also be made by synthetic means using techniques well known to skilled persons such as solid phase synthesis. Various techniques for chemical synthesising peptides are reviewed by Borgia and Fields, 2000, TibTech 18:243-251 and described in detail in the references contained therein.

The peptide can be coupled directly to the cytokine or indirectly through a spacer, which can be a single amino acid, an amino acid sequence or an organic residue, such as 6-aminocapryl-N-hydroxysuccinimide. The coupling procedures are known to those skilled in the art and comprise genetic engineering or chemical synthesis techniques.

The peptide ligand preferably is linked to the cytokine N-terminus thus minimizing any interference in the binding of the modified cytokine to its receptor. Alternatively, the peptide can be linked to amino acid residues which are amido- or carboxylic-bonds acceptors, naturally occurring on the molecule or artificially inserted with genetic engineering techniques. The modified cytokine is preferably prepared by use of a cDNA comprising a 5'-contiguous sequence encoding the peptide.

According to a preferred embodiment, there is provided a conjugation product between TNF and the CNGRC sequence. More preferably, the amino-terminal of TNF is linked to the CNGRC peptide through the spacer G (glycine).

The resulting product (NGR-TNF), proved to be more active than TNF on RMA-T lymphoma animal models. Furthermore, animals treated with NGR-TNF were able to reject further tumorigenic doses of RMA-T or RMA cells. The increase in the antitumoral activity, as compared with normal TNF, could be observed in immunocompetent animals but not in immunodeficient animals. This indicates that the increase in the antitumoral activity of TNF conjugated with "NGR" peptides is due to an enhanced immune response rather than to a direct cytotoxic activity of the conjugate.

It has also been demonstrated that the in vivo immune effects induced by NGR-TNF are directly related to the CD13 receptor. It has, for example, been observed that antibody against the CD 13 receptor as well as the GNGRC ligand compete with NGR-TNF in vivo, thus suggesting a mechanism of receptor targeting by NGR-TNF.

The therapeutic index of the TNF/CD13 ligand conjugates can be further improved by using a mutant form of TNF capable of selectively binding to one of the two TNF receptors, p75TNFR and p55TNFR. Said TNF mutant can be obtained by site-directed mutagenesis (Loetscher, H., et al., Human tumor necrosis factor alpha (TNF alpha) mutants with exclusive specificity for the 55-kDa or 75 kDa TNF receptors. J. Biol. Chem. 1993.268:26350-7 and Van Ostade, X., et al., Human TNF mutants with selective activity on the p55 receptor. Nature 1993.361:266-9.).

The pharmacokinetic of the modified cytokines according to the invention can be improved by preparing polyethylene glycol derivatives, which allow to extend the plasmatic half-life of the cytokines themselves.

A further embodiment of the invention is provided by bifunctional derivatives in which the cytokines modified with the CD 13 ligand are conjugated with antibodies, or their fragments, against tumoral antigens or other tumor angiogenic markers, e. g. (xv integrins, metalloproteases or the vascular growth factor, or antibodies or fragments thereof directed against components of the extracellular matrix, such as anti-tenascin antibodies or anti-fibronectin EDB domain. The preparation of a fusion product between TNF and the hinge region of a mAb against the tumor-associated TAG72 antigen expressed by gastric and ovarian adenocarcinoma has recently been reported (Yang, J., et al., A genetically engineered single-chain FV/TNF molecule possesses the anti-tumor immunoreactivity of FV as well as the cytotoxic activity of tumor necrosis factor. Mol. Immunol. 1995.32:873-81).

A further embodiment of the invention is provided by the tumoral pre-targeting with the biotin/avidin system. According to this approach, a ternary complex is obtained on the tumoral antigenic site, at different stages, which is formed by 1) biotinylated mAb, 2) avidin (or streptavidin) and 3) bivalent cytokine modified with the CD13 ligand and biotin. A number of papers proved that the pre-targeting approach, compared with conventional targeting with immunoconjugates, can actually increase the ratio of active molecule homed at the target to free active molecule, thus reducing the treatment toxicity (Paganelli, G., et al., Three-step monoclonal antibody tumor targeting in carcinoembryonic antigenpositive patients. Cancer Res. 1991. 51:5960-6; Paganelli, G., et al., Clinical application of the avidin-biotin system for tumor targeting. In D. Goldenberg (Ed. Cancer therapy with radiolabeled antibodies. CRC Press, Boca Raton, 1995. P. 239-253; Modorati, G., et al., Immunoscintigraphy with three step monoclonal pretargeting technique in diagnosis of uveal melanoma: preliminary results. Br. J. Ophtalm. 1994.78:19-23; Colombo, P., et al., Immunoscintigraphy with anti-chromogranin A antibodies in patients with endocrine/neuroendocrine tumors. J. Endocr. Invest. 1993.16:841-3). This approach produced favorable results with biotinylated TNF, which was capable of inducing cytotoxicity in vitro and decreasing the tumor cells growth under conditions in which normal TNF was inactive (Moro, M., et al., Tumor cell targeting with antibody-avidin complexes and biotinylated tumor necrosis factor alpha. Cancer Res. 1997.57:1922-8. And 26. Gasparri, A., et al., Tumor pretargeting with avidin improves the therapeutic index of biotinylated tumor necrosis factor alpha in mouse models. Cancer Res. 1999.59:2917-23.). The pre-targeting approach can also be carried out with a two-phase procedure by using a bispecific antibody which at the same time binds the tumoral antigen and the modified cytokine. The use of a bispecific antibody directed against a carcinoembryonic antigen and TNF has recently been described as a means for TNF tumoral pre-targeting (Robert, B., et al., 1996. Cytokine targeting in tumors using a bispecific antibody directed against carcinoembryonic antigen and tumor necrosis factor alpha. Cancer Res. 56:4758.).

According to a further embodiment, the invention comprises a TNF molecule conjugated to both a CD13 ligand and an antibody, or a fragment thereof (directly or indirectly via a biotin-avidin bridge), on different TNF subunits, where the antibody or its fragments are directed against an antigen expressed on tumor cells or other components of the tumor stroma, e. g. tenascin and fibronectin EDB domain. This results in a further improvement of the tumor homing properties of the modified cytokine and in the slow release of the latter in the tumor microenvironment through trimer-monomer-trimer transitions. As shown in previous works, in fact, the modified subunits of TNF conjugates can dissociate from the targeting complexes and reassociate so as to form unmodified trimeric TNF molecules, which then diffuse in the tumor microenvironment. The release of bioactive TNF has been shown to occur within 24-48 hours after targeting (Corti, A., et al., Tumor targeting with biotinylated tumor necrosis factor alpha: Structure activity relationships and mechanism of action on avidin pretargeted tumor cells. Cancer Res. 1998.58:3866-3872).

Peptides of the present invention may be administered therapeutically to patients. It is preferred to use peptides that do not consisting solely of naturally-occurring amino acids but which have been modified, for example to reduce immunogenicity, to increase circulatory half-life in the body of the patient, to enhance bioavailability and/or to enhance efficacy and/or specificity.

A number of approaches have been used to modify peptides for therapeutic application. One approach is to link the peptides or proteins to a variety of polymers, such as polyethylene glycol (PEG) and polypropylene glycol (PPG)—see for example U.S. Pat. Nos. 5,091,176, 5,214, 131 and 5,264,209.

Replacement of naturally-occurring amino acids with a variety of uncoded or modified amino acids such as D-amino acids and N-methyl amino acids may also be used to modify peptides Another approach is to use bifunctional crosslinkers, such as N-succinimidyl 3-(2 pyridyldithio) propionate, succinimidyl 6-[3-(2 pyridyldithio) propionamido] hexanoate, and sulfosuccinimidyl 6-[3-(2 pyridyldithio) propionamido] hexanoate (see U.S. Pat. No. 5,580,853).

It may be desirable to use derivatives of the peptides of the invention which are conformationally constrained. Conformational constraint refers to the stability and preferred conformation of the three-dimensional shape assumed by a peptide. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure.

The active conformation of the peptide may be stabilised by a covalent modification, such as cyclization or by incorporation of gamma-lactam or other types of bridges. For example, side chains can be cyclized to the backbone so as create a L-gamma-lactam moiety on each side of the interaction site. See, generally, Hruby et al., "Applications of Synthetic Peptides," in Synthetic Peptides: A User's Guide: 259-345 (W. H. Freeman & Co. 1992). Cyclization also can be achieved, for example, by formation of cysteine bridges, coupling of amino and carboxy terminal groups of respective terminal amino acids, or coupling of the amino group of a Lys residue or a related homolog with a carboxy group of Asp, Glu or a related homolog. Coupling of the. alpha-amino group of a polypeptide with the epsilon-amino group of a lysine residue, using iodoacetic anhydride, can be also undertaken. See Wood and Wetzel, 1992, Int'l J. Peptide Protein Res. 39:533-39.

Another approach described in U.S. Pat. No. 5,891,418 is to include a metal-ion complexing backbone in the peptide structure. Typically, the preferred metal-peptide backbone is based on the requisite number of particular coordinating groups required by the coordination sphere of a given complexing metal ion. In general, most of the metal ions that may prove useful have a coordination number of four to six. The nature of the coordinating groups in the peptide chain includes nitrogen atoms with amine, amide, imidazole, or guanidino functionalities; sulfur atoms of thiols or disulfides; and oxygen atoms of hydroxy, phenolic, carbonyl, or carboxyl functionalities. In addition, the peptide chain or individual amino acids can be chemically altered to include a coordinating group, such as for example oxime, hydrazino, sulfhydryl, phosphate, cyano, pyridino, piperidino, or morpholino. The peptide construct can be either linear or cyclic, however a linear construct is typically preferred. One example of a small linear peptide is Gly-Gly-Gly-Gly which has four nitrogens (an N4 complexation system) in the back bone that can complex to a metal ion with a coordination number of four.

A further technique for improving the properties of therapeutic peptides is to use non-peptide peptidomimetics. A wide variety of useful techniques may be used to elucidating the precise structure of a peptide. These techniques include amino acid sequencing, x-ray crystallography, mass spectroscopy, nuclear magnetic resonance spectroscopy, computer-assisted molecular modelling, peptide mapping, and combinations thereof. Structural analysis of a peptide generally provides a large body of data which comprise the amino acid sequence of the peptide as well as the three-dimensional positioning of its atomic components. From this information, non-peptide peptidomimetics may be designed that have the required chemical functionalities for therapeutic activity but are more stable, for example less susceptible to biological degradation. An example of this approach is provided in U.S. Pat. No. 5,811,512.

Techniques for chemically synthesising therapeutic peptides of the invention are described in the above references and also reviewed by Borgia and Fields, 2000, TibTech 18:243-251 and described in detail in the references contained therein.

For use in therapy, the modified cytokines of the invention will be suitably formulated in pharmaceutical preparations for the oral or parenteral administration. Formulations for the parenteral administration are preferred, and they comprise injectable solutions or suspensions and liquids for infusions. For the preparation of the parenteral forms, an effective amount of the active ingredient will be dissolved or suspended in a sterile carrier, optionally adding excipients such as solubilizers, isotonicity agents, preservatives, stabilizers, emulsifiers or dispersing agents, and it will be subsequently distributed in sealed vials or ampoules.

In more detail, conjugates of the invention, including polypeptides and polynucleotides, may preferably be combined with various components to produce compositions of the invention. Preferably the compositions are combined with a pharmaceutically acceptable carrier, diluent or excipient to produce a pharmaceutical composition (which may be for human or animal use). Suitable carriers and diluents include isotonic saline solutions, for example phosphate-buffered saline. Details of excipients may be found in The Handbook of Pharmaceutical Excipients, 2nd Edn, Eds Wade & Weller, American Pharmaceutical Association. The composition of the invention may be administered by direct injection. The composition may be formulated for parenteral, intramuscular, intravenous, subcutaneous, intraocular, oral or transdermal administration.

The composition may be formulated such that administration daily, weekly or monthly will provide the desired daily dosage. It will be appreciated that the composition may be conveniently formulated for administrated less frequently, such as every 2, 4, 6, 8, 10 or 12 hours.

Polynucleotides/vectors encoding polypeptide components may be administered directly as a naked nucleic acid construct, preferably further comprising flanking sequences homologous to the host cell genome.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example Lipofectam™ and Transfectam™). Typically, nucleic acid constructs are mixed with the transfection agent to produce a composition.

Preferably the polynucleotide or vector of the invention is combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular or transdermal administration.

The routes of administration and dosage regimens described are intended only as a guide since a skilled practitioner will be able to determine readily the optimum route of administration and dosage regimens for any particular patient and condition.

The preparation of cytokines in form of liposomes can improve the biological activity thereof. It has, in fact, been observed that acylation of the TNF amino groups induces an increase in its hydrophobicity without loss of biological activity in vitro. Furthermore, it has been reported that TNF bound to lipids has unaffected cytotoxicity in vitro, immunomodulating effects and reduced toxicity in vivo (Debs, R. J., et al., Liposome-associated tumor necrosis factor retains bioactivity in the presence of neutralizing anti-tumor necrosis factor antibodies. J. Immunol. 1989.143:1192-7; Debs, R. J., et al., Immunomodulatory and toxic effects of free and liposome-encapsulated tumor necrosis factor alpha in rats. Cancer Res. 1990.50:375-80.).

The maximum tolerated dose of bolus TNF in humans is 218-410 pg/m$^2$ (32. Fraker, D. L., Alexander, H. R. & Pass, H. I., 1995. Biologic therapy with TNF: systemic administration and isolation-perfusion. In Biologic therapy of cancer. principles and practice, De Vita, V., Hellman, S. & Rosenberg, S. (eds) pp. 329-345. J. B. Lippincott Company: Philadelphia.) about 10-fold lower than the effective dose in animals. Based on data from murine models it is believed that an at least 10 times higher dose is necessary to achieve anti-tumor effects in humans (Schraffordt Koops, et al., Hyperthermic isolated limb perfusion with tumour necrosis factor and melphalan as treatment of locally advanced or recurrent soft tissue sarcomas of the extremities, Radiothepray & Oncology 1998.48:1-4; Hill, S., et al., Low-dose tumour necrosis factor alpha and melphalan in hyperthermic isolated limb perfusion. Br. J. Sugr. 1993. 80:995-7; Eggermont, A. M., et al., Isolated limb perfusion with tumor necrosis factor and melphalan for limb salvage in 186 patients with locally advanced soft tissue extremity sarcomas. The cumulative multicenter European experience. Ann. Surg. 1996.224:756-65.). In the first clinical study on hyperthermic isolated-limb perfusion, high response rates were obtained with the unique dose of 4 mg of TNF in combination with melphalan and interferon y (Lienard, D., et al., In transit metastases of malignant melanoma treated by high dose rTNF alpha in combination with interferon-gamma and melphalan in isolation perfusion. World Journal of Surgery 1992. 16:234-40.). Other works showed that interferon y can be omitted and that even lower doses of TNF can be sufficient to induce a therapeutic response (Hill, S., et al., Low-dose tumour necrosis factor alpha and melphalan in hyperthermic isolated limb perfusion. Br. J. Sugr. 1993.80: 995-7; Eggermont, A. M., et al., Isolated limb perfusion with tumor necrosis factor and melphalan for limb salvage in 186 patients with locally advanced soft tissue extremity sarcomas. The cumulative multicenter European experience. Ann. Surg. 1996.224:756-65.). As the two cytokines exert synergistic effects on endothelial cells, their combined, selective targeting thereon is likely to result in stronger anti-tumor activity thus allowing to overcome the problems of systemic toxicity usually encountered in cancer therapy with the same cytokines used in combination. Furthermore, it is known that TNF can decrease the barrier function of the endothelial lining vessels, thus increasing their permeability to macromolecules. Taking advantage of the lower toxicity of treatment with the modified TNF molecules according to the invention, and of their tumor vessels homing properties, an alternative application is their use to increase the permeability of tumor vessels to other compounds, either for therapeutic or diagnostic purposes. For instance the modified TNF can be used to increase the tumor uptake of radiolabelled antibodies or hormones (tumor-imaging compounds) in radioimmunoscintigraphy or radioimmunotherapy of tumors. Alternatively, the uptake of chemotherapeutic drugs, immunotoxins, liposomes carrying drugs or genes, or other anticancer drugs could also be increased, so that their antitumor effects are enhanced.

Accordingly, the cytokines of the invention can be used in combined, separated or sequential preparations, also with other diagnostic or therapeutic substances, in the treatment or in the diagnosis of cancer.

The present invention relates to the use of a combination of the modified TNF, and IFNy. This combination can be used in combined, separated or sequential preparations. Advantageously the combination is also with other diagnostic or therapeutic substances, in the treatment or in the diagnosis of cancer, such as doxorubicin and mephalan. Thus the present invention provides a pharmaceutical composition comprising a combination of the modified TNF and IFNy, and optionally another tumor-diagnostic or anti-tumor therapeutic substance. Again, this combination can be used in combined, separated or sequential preparations.

In the patent application number PCT/IB03/02187, it was found that targeted delivery of picogram doses of cytokines enhances the penetration of chemotherapeutic drugs, providing a novel and surprising strategy for increasing the therapeutic index of chemotherapeutic drugs. Patent application number PCT/IB03/02187 is hereby incorporated by reference in its entirety. In more detail, it was found that delivery of very low doses of cytokines to tumors and the tumor-associated environment including tumor vasculature represents a new approach to avoiding negative feedback mechanisms and to preserve its ability to alter drug-penetration barriers.

The composition of the present invention may be formulated for parenteral, intramuscular, intravenous, subcutaneous, intraocular, oral or transdermal administration. In one embodiment of this aspect of the present invention, a conjugate of the present invention may be administered at a dose of from in the range of 0.5 to 500 ng/kg, preferably in the range of 1 to 50 ng/kg, more preferably in the range of 5 to 15 ng/kg.

In an alternative embodiment of this aspect of the invention there is provided a pharmaceutical composition comprising a conjugate of the present invention in combination with IFNy, wherein the conjugate is present in an amount such that the conjugate or a metabolite thereof is provided to the blood plasma of the subject to be treated in an amount of no greater than about 35,000 ng/day, preferably about 3,500 ng/day, more preferably about 1,000 ng/day.

The above dosage relates to a dosage for a 70 kg subject. A person skilled in the art would readily be able to modify the recited dosage for a subject having as mass other than 70 kg.

The routes of administration and dosage regimens described are intended only as a guide since a skilled practitioner will be able to determine readily the optimum route of administration and dosage regimens for any particular patient and condition.

Another aspect of the invention regards the cDNA encoding for the conjugated cytokines herein disclosed, which can be prepared from the cytokines cDNA by addition of a 5'- or 3'-contiguous DNA sequence encoding for the CD13 ligand, preferably for the homing peptides described above. The combined cDNA can be used as such or after insertion in vectors for gene therapy. The preparation and therapeutic applications of suitable vectors is disclosed in (Mizuguchi, H., et al., Tumor necrosis factor alpha-mediated tumor regression by the in vivo transfer of genes into the artery that leads to tumor. Cancer Res. 1998.58:5725-30.), which is hereby incorporated by reference.

Polynucleotides for use in the invention comprise nucleic acid sequences encoding the polypeptide conjugate of the invention. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

Polynucleotides of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5'ends of the molecule. For the purposes of the present invention, it is to be understood that the polynucleotides described herein may be modified by any method available in the art. Such modifications may be carried out in order to enhance the in vivo activity or life span of polynucleotides of the invention.

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example insect Sf9 cells.

Preferably, a polynucleotide of the invention in a vector is operably linked to a control sequence that is capable of providing for the expression of the coding sequence by the host cell, i. e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors of the invention may be transformed or transfected into a suitable host cell as described below to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term "promoter" is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of a-actin, b-actin, tubulin) or, alternatively, a tissue-specific manner (such as promoters of the genes for pyruvate kinase). Tissue-specific promoters specific for certain cells may also be used. They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter. It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Vectors and polynucleotides of the invention may be introduced into host cells for the purpose of replicating the vectors/polynucleotides and/or expressing the proteins of the invention encoded by the polynucleotides of the invention.

Although the proteins of the invention may be produced using prokaryotic cells as host cells, it is preferred to use eukaryotic cells, for example yeast, insect or mammalian cells, in particular mammalian cells.

Vectors/polynucleotides of the invention may introduced into suitable host cells using a variety of techniques known in the art, such as transfection, transformation and electroporation. Where vectors/polynucleotides of the invention are to be administered to animals, several techniques are known in the art, for example infection with recombinant viral vectors such as retroviruses, herpes simplex viruses and adenoviruses, direct injection of nucleic acids and biolistic transformation.

Host cells comprising polynucleotides of the invention may be used to express conjugates of the invention. Host cells may be cultured under suitable conditions which allow expression of the polypeptides and conjugates of the invention. Expression of the products of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Conjugates of the invention can be extracted from host cells by a variety of techniques known in the art, including enzymatic, chemical and/or osmotic lysis and physical disruption.

The present invention will be illustrated by means of non-limiting examples in reference to the following figures.

FIG. 1: Overall trial design. Details on endpoints and statistics in the two phases are reported. NGR-hTNF/RCHOP regimen was different in the two phases for organizational and clinical reasons.

Figure 2:
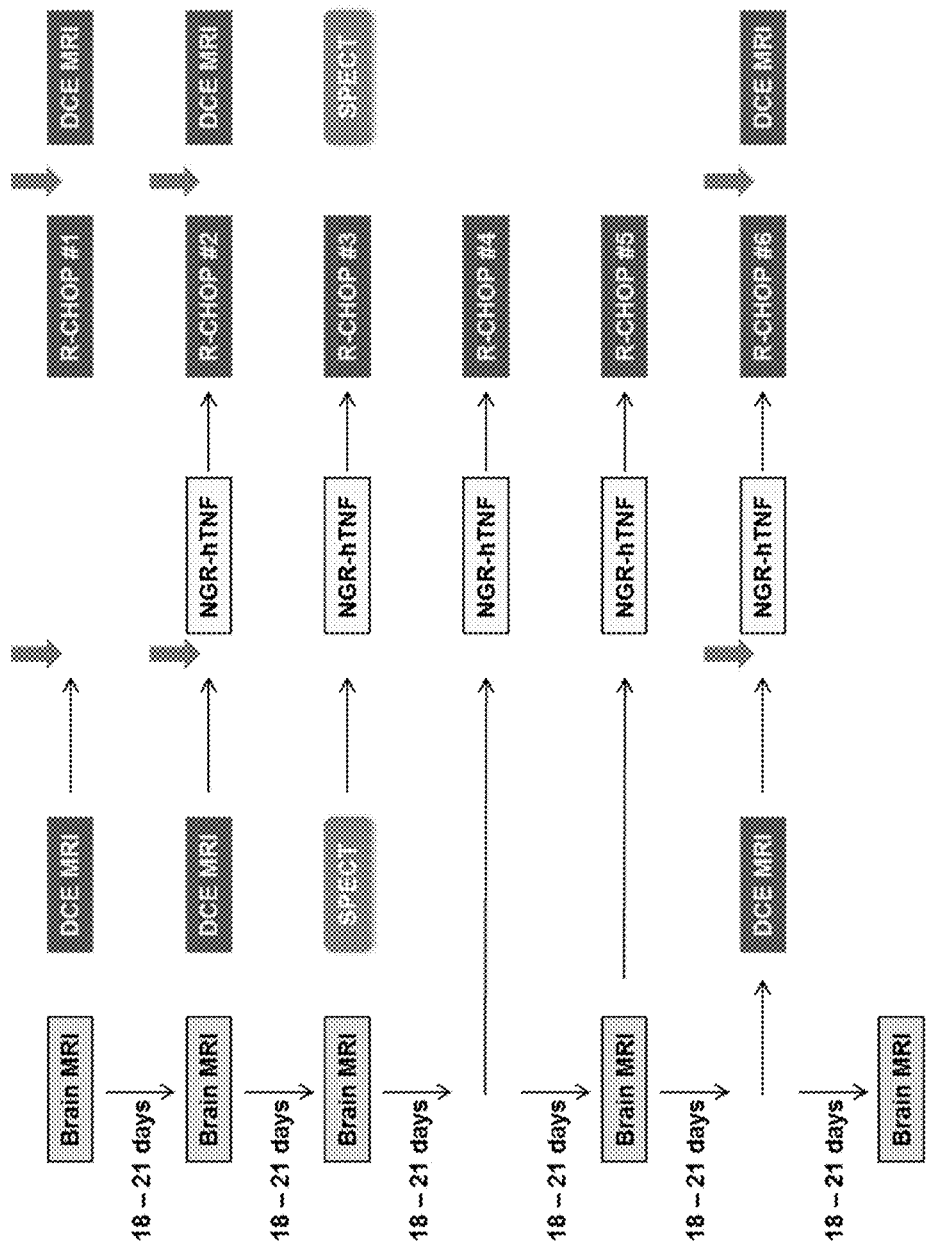

FIG. 2: Design of explorative phase (first ten patients). Enrolled patients received a first course of R-CHOP that was not preceded by NGR-hTNF, while the other five courses were preceded by NGR-hTNF. Brain MRI represents Gadolinium-enhanced magnetic resonance imaging performed for response assessment, while DCE-MRI is the cerebral dynamic contrast-enhanced MRI used to assess changes in BBB permeability. SPECT is the single positron emission computerized tomography performed before and after the 3rd course to assess changes in BBB permeability. Arrows represent collection of CSF and plasma samples.

Figure 3:
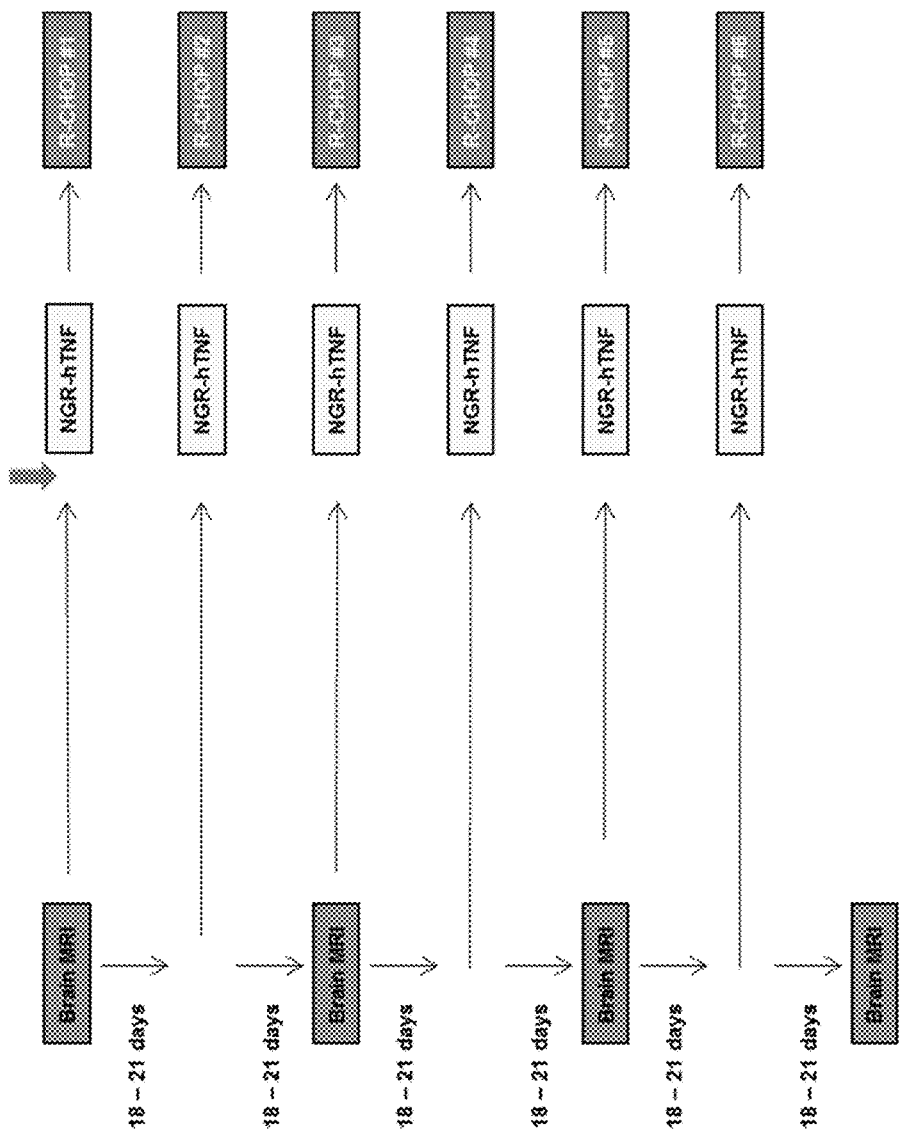

FIG. 3: Design of expansion phase (second 18 patients). Enrolled patients received six courses of NGR-hTNF/R-CHOP. Brain MRI represents Gadolinium-enhanced magnetic resonance imaging performed for response assessment. Arrow represents collection of baseline CSF and plasma samples.

Figure 4:
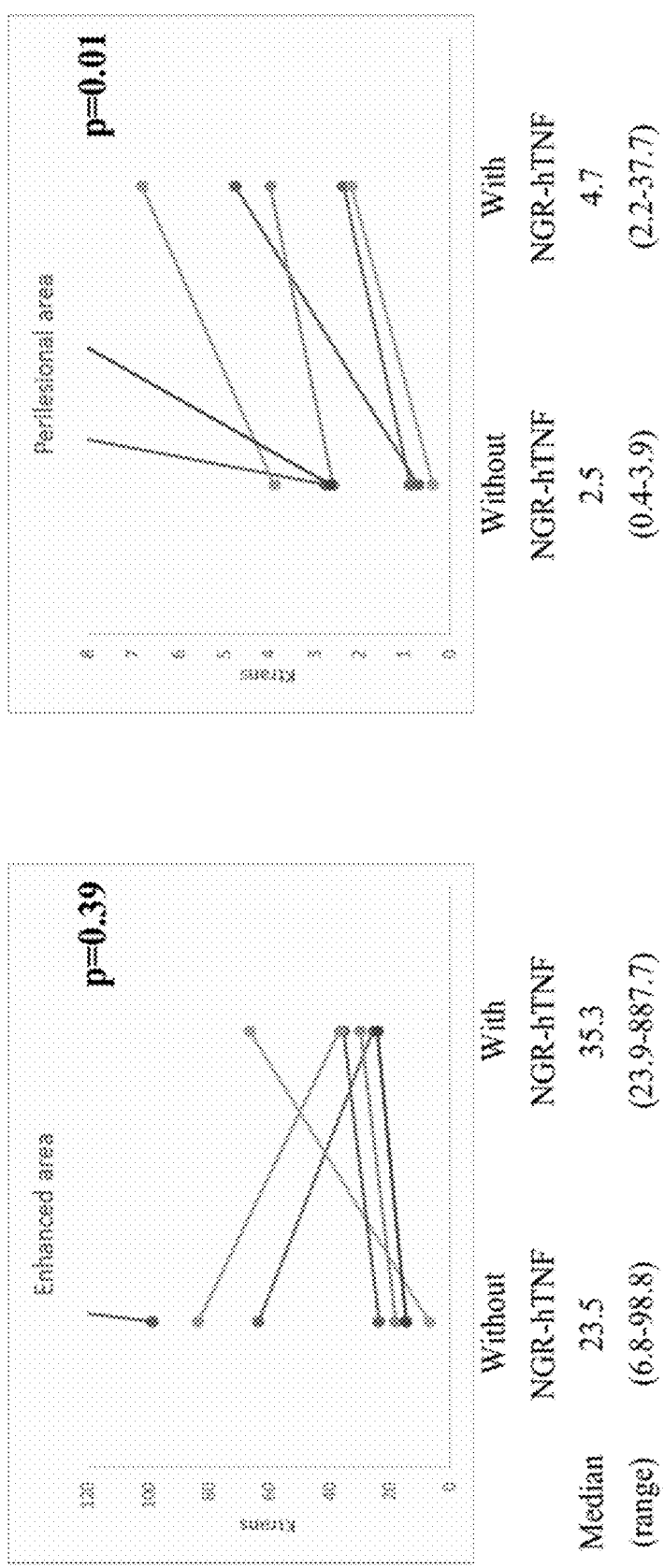

FIG. 4: Changes in BBB permeability assessed by DCE-MRI in responders. Changes in the enhanced areas are represented on the left and in the perilesional areas on the right; results are expressed in Ktrans. Values at the first course (without NGR-hTNF) and second course (with NGR-hTNF) for each patient are linked with a line. Median and range values per subgroup are reported at the bottom of each graphic.

Figure 5:
Figure 5:
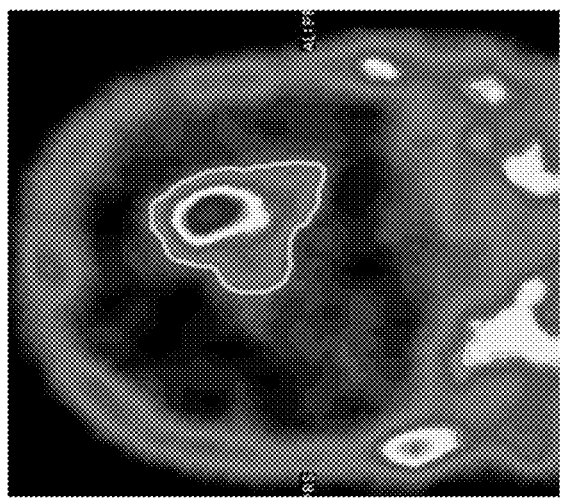
Figure 5:
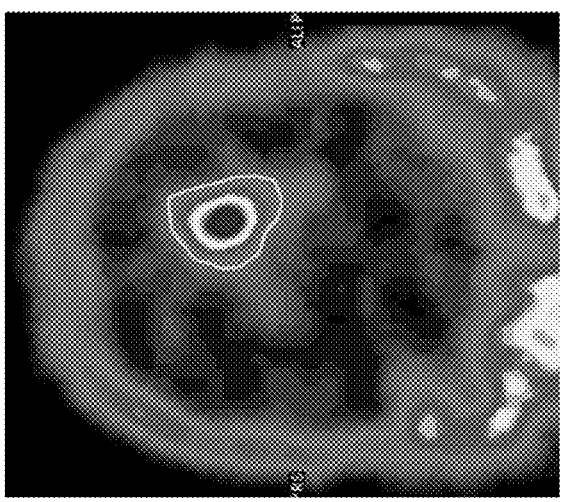

FIG. 5: An example of increase of $^{99m}$Tc-DTPA uptake after the infusion of NGR-hTNF followed by R-CHOP at the 3rd course of treatment. The volume of ≥30% $^{99m}$Tc-DTPA uptake is contoured in two SPECT studies performed before (left imagine-blue line) and after (middle imagine-green line) administration of NGR-hTNF and R-CHOP. Comparison of contoured volumes are represented in the gadolinium-enhanced T1-weighted MRI showing the tumor (right imagine). The volume of interest before and after NGR-hTNF/R-CHOP delivery was 22 cm³ and 40 cm³ respectively.

Figure 6:
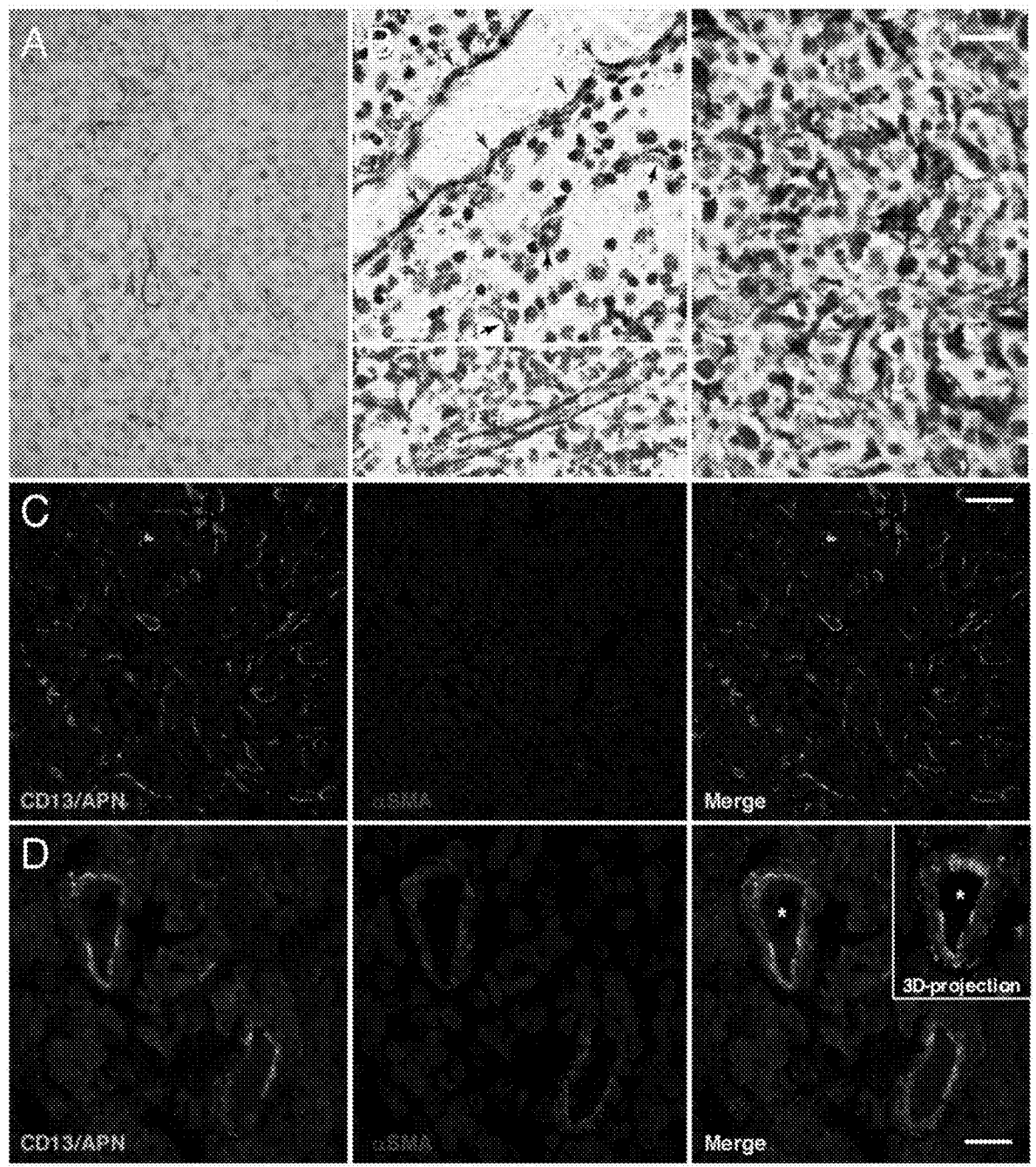

FIG. 6: Expression of CD13 by the endothelial lining of tumor vasculature. A) Immunohistochemical analysis of CD13 expression within lymphomatous component of diagnostic brain biopsy of an enrolled patient. Staining was performed using the anti-CD13 monoclonal antibody SP187 alone (brown signal, 400×). B) Immunohistochemical analysis of CD13 and αSMA (a marker of pericytes). The co-staining was performed with the anti-CD13 monoclonal antibody SP187 (brown) and the anti-αSMA monoclonal antibody 1A4 (red). Black arrows indicate CD13-positive vessels; red arrows indicate αSMA-positive perivascular cells (bar 20 μm; 630×). Left panels: representative photograph of areas with large vessels with pericyte coverage (red) and some microvessels, showing CD13 staining (brown) also in the absence of pericytes. Right: representative photograph of an area with several CD13-positive microvessels (brown). C-D) Confocal immunofluorescence analysis of a tissue section stained with a polyclonal anti-CD13 antibody (green) and with the anti-αSMA antibody 1A4 (red) (400×, bar: 50 μm). Inset: 3D projection of CD13 and αSMA staining of a mature vessel (asterisk) (400×, bar: 25 μm) showing that CD13 was expressed on the luminal side of the vascular endothelium.

Figure 7:
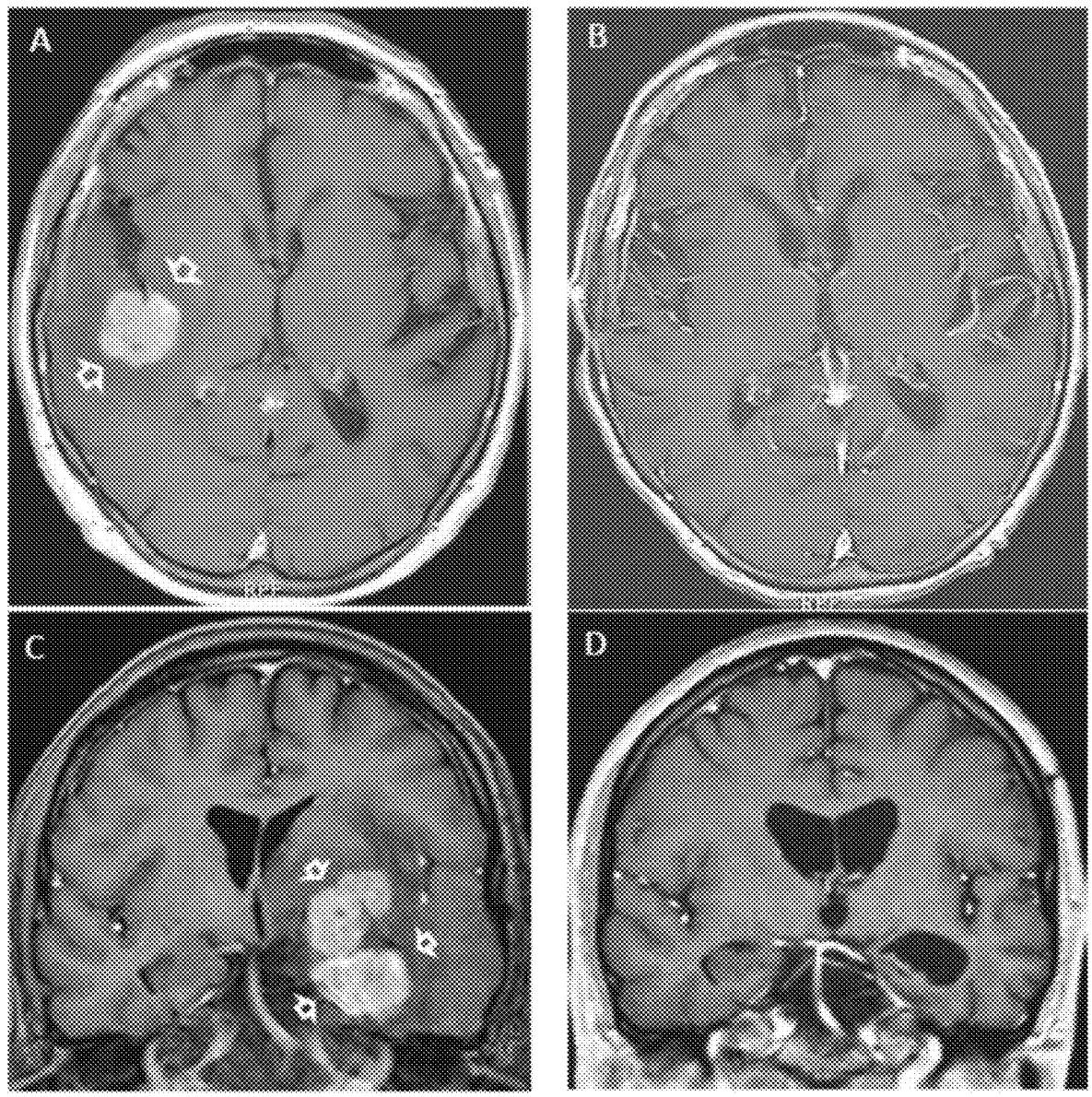

FIG. 7: Examples of responses to R-CHOP preceded by NGR-hTNF.

A) Gadolinium-enhanced T1 weighted scan shows a large homogeneous enhancing lesion in the right parietal lobe (arrows) in a 65-year-old gentleman at the second relapse after high-dose-methotrexate and after salvage high-dose-ifosfamide-based therapy plus whole-brain irradiation. B) Tumor regression after four courses of experimental treatment. C) Gadolinium-enhanced T1 weighted scan shows a large polylobate, enhancing lesion infiltrating the basal ganglia, diencephalon and left temporal lobe (arrows) in a 39-year-old gentleman with PCNSL refractory to prior high-dose-methotrexate-based chemoimmunotherapy. D) Tumor regression after four courses of experimental treatment.

Figure 8:
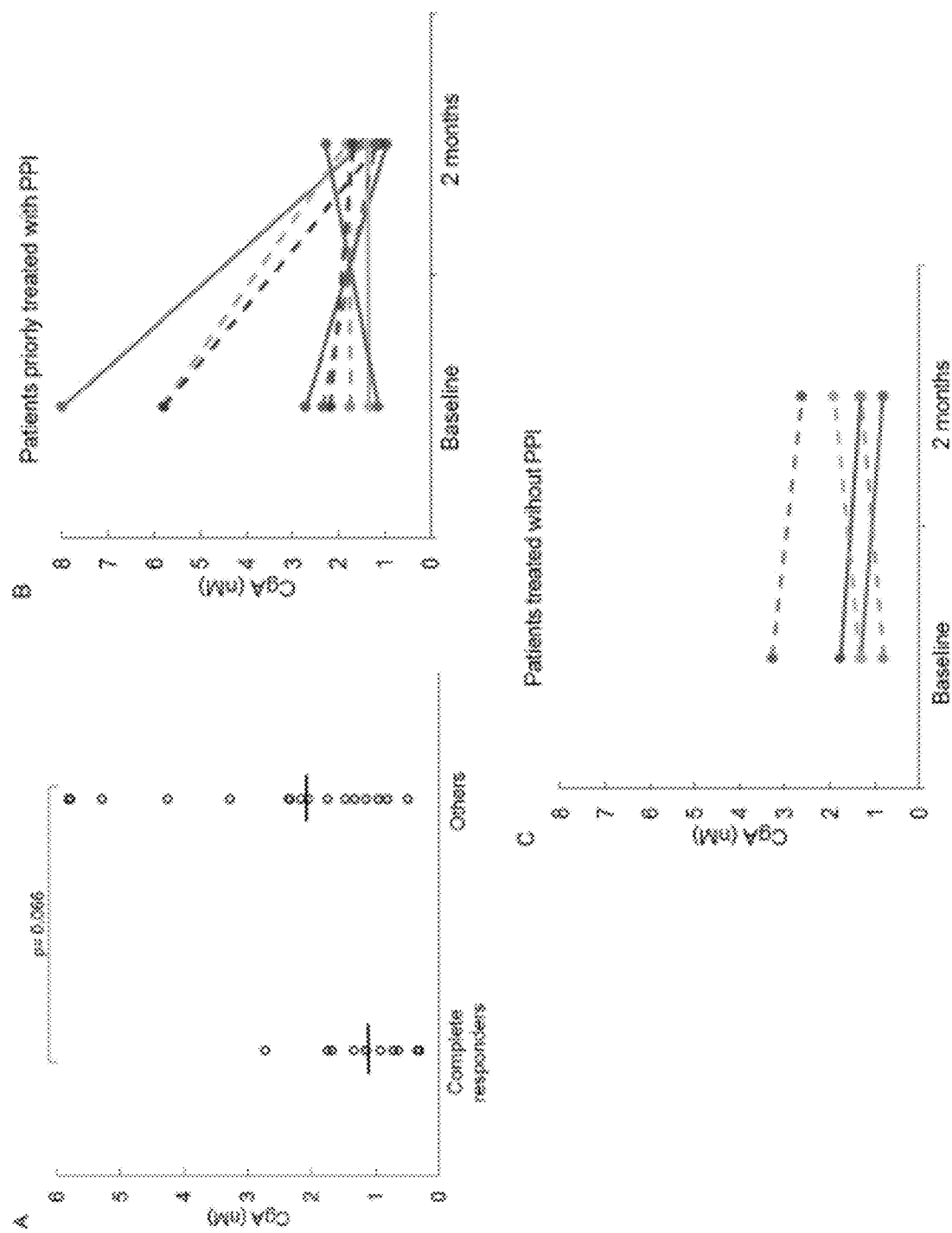

FIG. 8: Chromogranin A (CgA) plasma levels, PPI therapy and responses

A) Relationship between CgA plasma levels and response to NGR-hTNF/R-CHOP. Baseline plasma levels of CgA of patients who achieved a complete remission (n=12) and patients who did not (others, n=16) are shown. Median values (range) of CgA levels were 1.14 nM (0.29-2.72) and 2.10 nM (0.47-5.81), respectively (p=0.066). B & C) Changes in CgA plasma levels after proton pump inhibitors (PPI) interruption.

The comparison of CgA concentrations in plasma samples collected at trial registration (baseline) and before the $3^{rd}$ course (2 months) showed level reduction in some patients after PPI interruption (B), while the values remained stable in patients who had not received this drug (C). No differences were detected between patients achieving a complete remission (continued lines) or a partial response (dotted lines).

Figure 9:
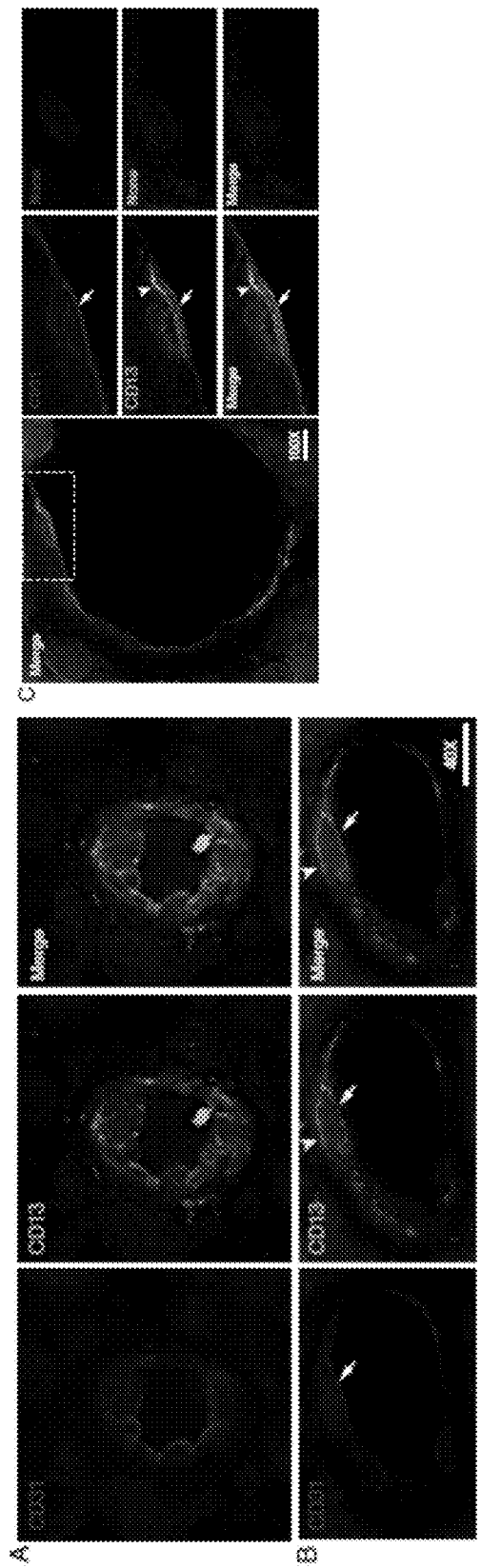
Figure 9:
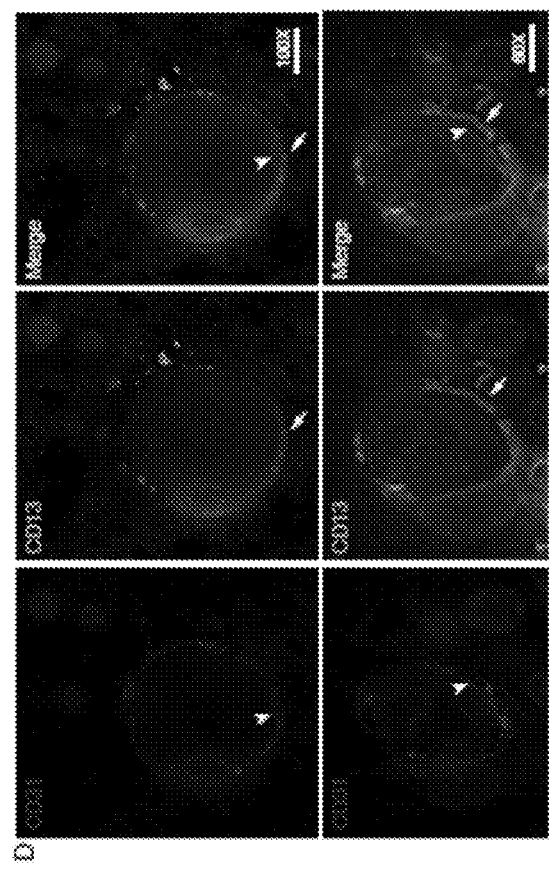

FIG. 9: Expression of CD13 by endothelial cells and pericytes in primary CNS lymphoma vasculature High-resolution wide field co-immunofluorescence analysis of PCNSL tissue sections from two enrolled patients stained with a polyclonal anti-CD13 antibody (green) and with a polyclonal anti-CD31, a marker of endothelial cells (red). Nuclear staining with DAPI (blue).

A-C) Examples of vessels with CD13-positive endothelial cells (arrows, yellow in the merged figure) and CD13-positive mural cells (arrowheads, green, likely pericytes). See also Supplemental Movie 1 for Z-stack images of the vessel reported in panel A.

B) Central panels: electronic enlargement of the highlighted area (dashed rectangle) of the vessel shown in the left panel. B) Right panels: controls performed on a consecutive section with secondary antibodies alone, showing lack of staining.

D) Examples of vessels with CD13-positive mural cells and CD13-negative endothelial cells (green and red, arrowheads and arrows, respectively, in the merged figure). Scale bar, 5 μm; magnification is shown in each panel.

Figure 10:
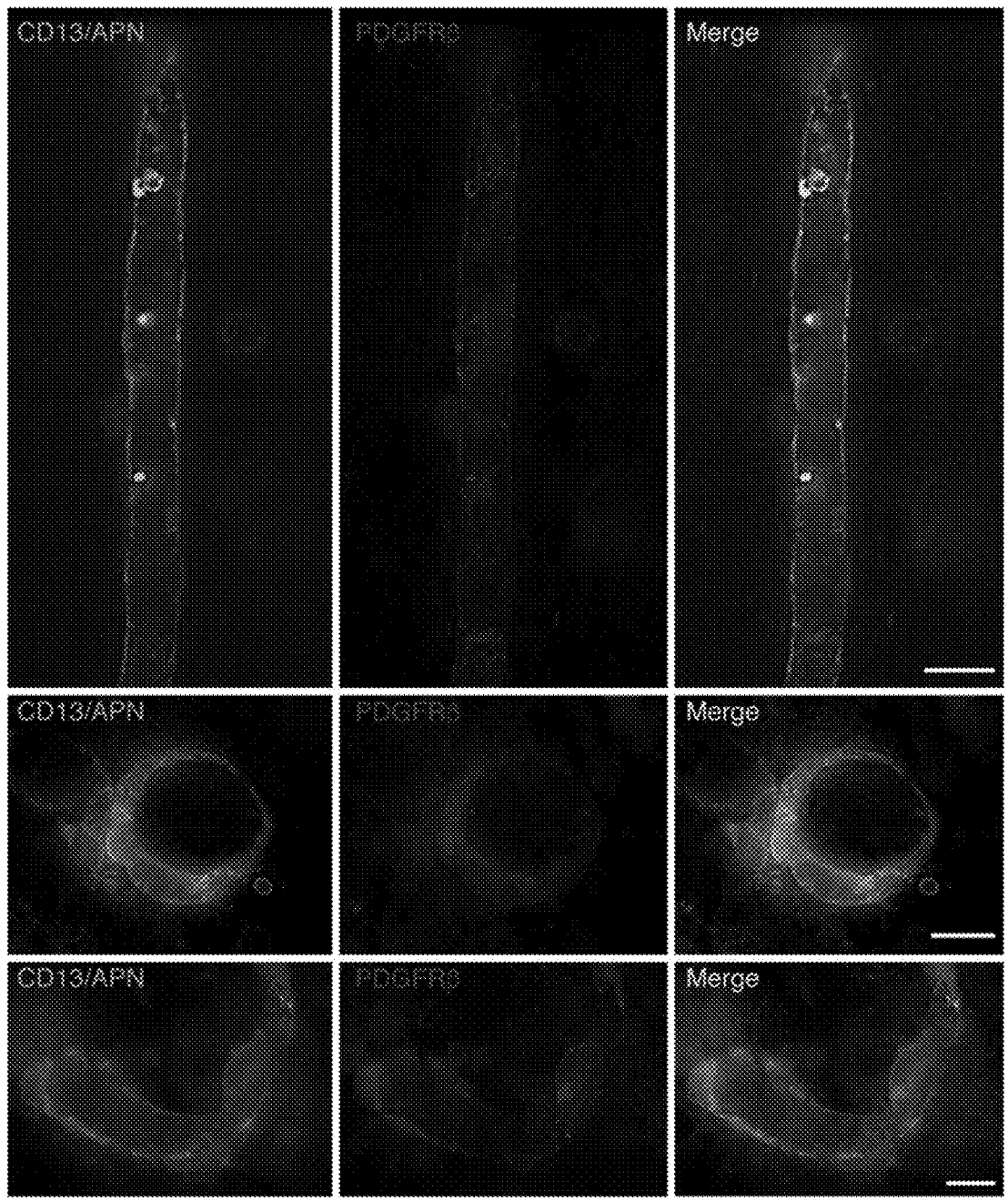

FIG. 10. CD13 and PDGFRβ expression in PCNSL vasculature.

High-resolution wide field co-immunofluorescence analysis of a PCNSL tissue section of an enrolled patient stained with a polyclonal anti-CD13 antibody (green) and with a polyclonal anti-PDGFRB, a marker of pericytes (red). Nuclear staining with DAPI (blue). Representative staining of 3 different vessels is shown. Magnification, 60×; scale bar, 10 μm.

DETAILED DESCRIPTION OF THE INVENTION

Patients and Methods

Study Population and Selection Criteria

The "INGRID" study is a single-arm phase II trial focused on an experimental treatment consisting of six courses of R-CHOP preceded by NGR-hTNF infusion in HIV-negative patients with relapsed or refractory PCNSL (EUDRACT: 2014-001532-11—clinicaltrials.gov NCT03536039). The trial has two distinct parts (FIG. 1): the first one is focused on feasibility and "proof of principle" of the effects of NGR-hTNF on BBB permeability; the second part is focused on activity and tolerability of the experimental treatment. Selection criteria were: 1) histologically-proven diagnosis of DLBCL according to the WHO criteria[17]; 2) disease exclusively localized in the CNS, cranial nerves, meninges, and/or eyes both at first diagnosis and trial registration; 3) lymphoma relapsed after or refractory to prior chemotherapy containing high-dose methotrexate; 4) measurable disease; 5) age 18-80 years; 6) ECOG performance status score ≤3. Patients with prior organ transplant or other forms of immunosuppression, with HBV, HCV and/or HIV infections, or other malignancies were excluded. Any kind of consolidation therapy (i.e., whole-brain radiotherapy -WBRT-, autologous stem cell transplantation -ASCT-, oral drug maintenance) during prior lines was admitted. Before trial registration, histopathological diagnostic specimens and neuroimaging exams performed at diagnosis and relapse were centrally reviewed, and patients were assessed by physical & neurological examination, haemogram and biochemical serum profiles (including viral markers: HIV, HBV, HCV), echocardiography, enhanced neck, thorax and abdomen CT scan, bone marrow biopsy, contrast-enhanced brain MRI, CSF examination, ophthalmologic evaluation, and [18]FDG-PET. Risk was defined according to the IELSG score both at diagnosis and trial registration[18]. Written informed consent was obtained from each patient once eligibility was confirmed and after patient's review of the protocol contents. This trial conformed to the Declaration of Helsinki and was approved by the IRBs of the San Raffaele Scientific Institute of Milano, Italy.

Explorative Phase: Design and Treatment

Design of explorative phase is summarized in FIG. 2. The first ten enrolled patients received a first course of R-CHOP that was not preceded by NGR-hTNF, while the other five courses were preceded by NGR-hTNF (Table 1).

TABLE 1

Treatment regimens used in the Exploratory and Expansion phases

| Exploratory phase R-CHOP (course #1) | |
|---|---|
| Day 0: | Rituximab 375 mg/m$^2$ as IV infusion |
| Day 1: | Cyclophosphamide 750 mg/m$^2$ as IV bolus<br>Doxorubicin 50 mg/m$^2$ as IV bolus<br>Vincristine 1.4 mg/m$^2$ (max. 2 mg) as IV bolus |
| Days 2-6: | Prednisone 75 mg/d oral |

TABLE 1-continued

Treatment regimens used in the Exploratory and Expansion phases

| NGR-hTNF/R-CHOP (courses #2 to 6) | |
|---|---|
| Day 0: | Rituximab 375 mg/m$^2$ as IV infusion |
| Day 1: | NGR-hTNF 0.8 μg/m$^2$ as 1-hour infusion<br>(one hour before CHOP)<br>Cyclophosphamide 750 mg/m$^2$ as IV bolus<br>Doxorubicin 50 mg/m$^2$ as IV bolus<br>Vincristine 1.4 mg/m$^2$ (max. 2 mg) as IV bolus |
| Days 2-6: | Prednisone 75 mg/d oral |

In other words, enrolled patients received six courses of R-CHOP21 preceded by NGR-hTNF. Treatment was delivered in two days: rituximab at 375 mg/m$^2$ was delivered the day 1, NGR-hTNF at a dose of 0.8 μg/m$^2$ was delivered by a 1-hour infusion in day 2, two hours before CHOP drugs. Per protocol, the first course of R-CHOP was not preceded by NGR-hTNF in the first ten patients[14]. The rationale for the timing and administration schedule of NGR-hTNF has been previously reported[14]. Patients enrolled in the expansion phase (after the first 10 cohort) received therefore the six courses of R-CHOP preceded by NGR-hTNF. Oral or intravenous acetaminophen/paracetamol at a dose of 1.000 mg were delivered as prophylaxis of infusion-related reactions, 30 to 60 minutes prior starting each infusion of NGR-hTNF. Steroids, other than the five days of prednisone, were avoided, and, when clinically indicated, they were interrupted the day of NGR-hTNF infusion. Therapy with PPIs was avoided and replaced with $H_2$-blockers (i.e. ranitidine) at trial registration.

Patients who completed the six planned courses and achieved a complete (CR) or partial (PR) response were evaluated for consolidative therapy. Per protocol, and accordingly to prior treatments, WBRT 30-36 Gy, carmustine-thiotepa-conditioned ASCT or oral lenalidomide maintenance were allowed.

Expansion Phase

NGR-hTNF/R-CHOP (Courses #1 to 6)

Day 1: Rituximab 375 mg/m$^2$ as IV infusion

NGR-hTNF 0.8 μg/m$^2$ as 1-hour infusion immediately after rituximab

Cyclophosphamide 750 mg/m$^2$ as IV bolus one hour after NGR-hTNF

Doxorubicin 50 mg/m$^2$ as IV bolus immediately after cyclophosphamide

Vincristine 1.4 mg/m$^2$ (max. 2 mg) as IV bolus immediately after doxorubicin

Days 2-6: Prednisone 75 mg/d oral

R-CHOP was delivered at conventional doses: rituximab 375 mg/m$^2$ as intravenous (IV) infusion on day 0, followed by cyclophosphamide 750 mg/m$^2$ as IV bolus, doxorubicin 50 mg/m$^2$ as IV bolus and vincristine 1.4 mg/m$^2$ (max. 2 mg) as IV bolus on day 1; prednisone 75 mg/d oral on days 2-6. NGR-hTNF 0.8 μg/m$^2$ was delivered 2 hours before CHOP by a 1-hour infusion. Therapy with proton pump inhibitors was avoided as these drugs can increase chromogranin levels and eventually interfere with NGR-hTNF activity. H2-blockers (i.e. ranitidine) were allowed as gastro-protective therapy. Steroids other than the five days of prednisone were avoided, and, when clinically indicated, they were interrupted the day of NGR-hTNF infusion.

Expansion Phase: Design and Treatment

Design of expansion phase is summarized in FIG. 3. The other 18 enrolled patients (after the first 10) received a six courses of R-CHOP preceded by NGR-hTNF (Table 1). Other difference regards the delivery of all the drugs in a single day, that is: rituximab 375 mg/m² as intravenous (IV) infusion followed by NGR-hTNF 0.8 µg/m² by a 1-hour infusion and CHOP drugs delivered 2 hours later (cyclophosphamide 750 mg/m² as IV bolus, doxorubicin 50 mg/m² as IV bolus and vincristine 1.4 mg/m² [max. 2 mg] as IV bolus; prednisone 75 mg/d oral on days 2-6). Use of proton pump inhibitors and steroids followed the same above-mentioned recommendations. Patients who completed the six planned courses and achieved a complete (CR) or partial (PR) response during explorative or expansion phases were evaluated for consolidative therapy. Per protocol, and accordingly to prior treatments, WBRT 30-36 Gy, carmustine-thiotepa-conditioned ASCT or oral lenalidomide maintenance were allowed.

Drugs

Rituximab, cyclophosphamide, doxorubicin, vincristine, prednisone is any commercially or else available forms.

NGR-hTNF

A genetically engineered protein consisting of CNGRCG fused to the N-terminus of human tumor necrosis factor alpha of sequence:

```
                                        (SEQ ID No. 1)
CNGRCGVRSSSRTLSDKPVAHVVANPQAEGQL

QWLNRRANALLANGVELRDNQLVVPSEGLYLI

YSQVLFKGQGCPSTHVLLTHTISRIAVSYQTK

VNLLSAIKSPCQRETPEGAEAKPWYEPIYLGG

VFQLEKGDRLSAEINRPDYLDFAESGQVYFGI

IAL
``` expressed in *E. coli* cells.

NGR-hTNF analogs are described in WO 2004/041297 and WO 01/61017 incorporated by reference. For example, the analog is preferably a straight or cyclic peptide comprising the NGR motif, such as CNGRCVSGCAGRC (SEQ ID NO: 2), NGRAHA (SEQ ID NO: 3), GNGRG (SEQ ID NO: 4), cycloCVLNGRMEC (SEQ ID NO: 5) or cycloC-NGRC (SEQ ID NO: 6), or, more preferably, the peptide CNGRC (SEQ ID NO: 7).

Toxicity and Response Assessments

Treatment side effects were assessed separately for each chemotherapy course and graded according to the NCI-NCIC CTC version 3·0[19]. The worst toxicity per organ, per patient was considered. Periodic specialist controls, ECG, troponin levels determination, and echocardiography were performed before every treatment course to exclude cardiac toxicity. The impact of treatment on cognitive functions was not assessed by ad hoc tests.

All eligible patients were considered for response evaluation. Response was assessed by gadolinium-enhanced MRI of the brain performed on a 1.5 Tesla scanner after the $1^{st}$, $2^{nd}$, $4^{th}$, and $6^{th}$ course of treatment (FIGS. 2 and 3). In cases with concomitant positive CSF and/or vitreous, examination was performed after the $2^{nd}$, $4^{th}$ and $6^{th}$ courses. Response was defined according to the IPCG criteria[20] (Table 2).

TABLE 2

International PCNSL Collaborative Group Response Criteria

| Response | Neuroimaging | Steroid | Eye examination | CSF cytology |
|---|---|---|---|---|
| CR | No contrast enhancement | None | Normal | Negative |
| CRu | No contrast enhancement | Any | Normal | Negative |
|  | Minimal abnormality | Any | Minor RPE abnormality | Negative |
| PR | 50% decrease in lesions | Any | Minimal RPE abnormality or normal | Negative |
|  | No contrast enhancement | Any | Decrease in vitreous cells | Persistent/suspicious |
| PD | 25% increase in lesions Any new site | Any | Recurrent or new ocular disease | Recurrent/positive |

CR = complete response;
Cru = unconfirmed complete response;
RPE = retinal pigment epithelium;
PR = partial response;
PD = progressive disease Briefly, CR consisted of disappearance of all evidence of lymphoma; PR was a >50% decrease in tumour size; progressive disease (PD) was a >25% increase in tumour size or detection of any new lesion; all other situations were considered as stable disease (SD). As an important change in the IPCG criteria, a "response" was considered only whenever tumor regression was confirmed in two consecutive MRI; accordingly, every "response" required a minimum duration of 6-8 weeks. Response after the first course of R-CHOP did not drive therapeutic decision, whereas patients with PD at any of the following MRIs were considered "off study" and treated according to institutional guidelines. The maximum response recorded from treatment start was considered for analyses. The duration of response was measured from the date of maximum response to the date of objective progression, death for any cause or last visit of follow-up. After end of treatment, the disease was assessed every three months.

Biomarkers Assessment

Plasma levels of CgA and sTNF-R1 and -R2 were tested by ELISA on samples collected at the same time points of tumor response assessment.

Plasma levels of CgA and sTNF-Rs (receptors 1 and 2) were tested on samples collected at the same time points of tumor response assessment, i.e. before the first course of treatment, and after the second and the sixth courses. sTNF-Rs were tested using commercially available kits (DuoSet ELISAs, R&D Systems). CgA plasma levels were assessed by using a home-made ELISA kit[21], based on the use of the monoclonal antibody B4E11 in the capture step and an anti-CgA rabbit antiserum in the detection step.

The relationship between PPI therapy (yes vs. not) and plasma levels of CgA (continuous variable) and (continuous variable) was assessed by the U test of Mann-Whitney. The relationship between therapeutic response (CR vs. not CR) and plasma levels of CgA or sTNF-Rs was assessed by chi-square test, using cut-offs to distinguish subgroups with "low" and "high" plasma levels; cut-offs were chosen based on ROC curves.

The relationships between plasma levels of CgA or sTNF-Rs (continuous variables) and therapeutic response (CR vs. not CR) and PPI therapy (yes vs. not) were assessed by the U test of Mann-Whitney.

To characterize the expression of CD13 (the target of NGR) in PCNSL vasculature, we performed double immunofluorescence staining experiments on tumor tissue sections of registered patients with anti-CD13 and anti-CD31 (a marker of endothelial cells) antibodies and with anti-CD13 and anti-platelet-derived growth factor receptor-β (PDGFR-β; a marker of pericytes) antibodies.

Immunofluorescence Studies

The expression of CD13, CD31 and platelet-derived growth factor receptor-β (PDGFR-β) in tumor tissues was assessed by immunofluorescence techniques on paraffin-embedded specimens (10 μm thick) of diagnostic samples of registered patients. Immunofluorescence staining was performed, after antigen retrieval, using the anti-CD13/APN rabbit polyclonal antibody (1051-RP02, SinoBiological, 1:500), the anti-CD31/PECAM-1 sheep polyclonal antibody (a marker of endothelial cells, AF806, R&D System, 15 μg/ml), and the anti-PDGFR-β goat polyclonal antibody (a marker of pericytes, AF385, R&D System, 10 μg/ml). Antibodies were diluted with PBS containing 1% BSA, 5% normal horse serum, 0.1% Triton X-100, and incubated overnight at 4° C. After washing, the binding of anti-CD13 and anti-CD31 antibodies was detected using a mixture of secondary antibodies consisting of donkey anti-rabbit IgG-Alexa Fluor 488 (green, 4 μg/ml) and donkey anti-sheep IgG-Alexa Fluor 568 (red, 4 μg/ml) conjugates, for double staining of CD13 and CD31. The binding of anti-CD13 and anti-PDGFR-β antibodies was detected using a mixture of secondary antibodies consisting of donkey anti-rabbit IgG-Alexa Fluor 488 (green, 4 μg/ml) and donkey anti-goat IgG-Alexa Fluor 546 (red, 4 μg/ml) conjugates for double staining of CD13 and PDGFRβ. Nuclear staining was performed with DAPI (blue). Fluorescence signals were acquired using a high-resolution wide-field microscope (DeltaVision™ Ultra, GE healthcare, equipped with 40×/1.35, 60×/1.42 and 100×/1.4 objective lens. Z-stack acquisition was performed at 0.2 μm and 0.3 μm intervals (100× objective and 40× or 60× objective, respectively). Z-stacks were deconvoluted and processed using an in-built software. Images were extracted from Z-stacks using the Image J software.

Statistical Considerations

Overall response rate (ORR: CR and PR) was the primary endpoint, and the two-stage Simon Minimax design was used. The maximum ORR considered of low interest was 30% (in analogy with the rate reported in prior prospective trials focused on salvage treatment in PCNSL patients performed at inventors institution[22,23]), and the minimum ORR considered of interest was 50%; to demonstrate that difference, a total of 28 patients was needed (one-sided test; type I error 0.10; power 0.9). At the first step, 12 patients would be registered and, if at least four responses were observed, the study would have continued up to a total of 28 patients. If at least 12 responses were recorded, the experimental treatment would be declared active. Associations between responses and clinical and therapeutic variables were addressed by the Fisher exact test. Analysed variable were age (≤60 years vs. >60 years), LDH serum level (normal vs. high), CSF protein concentration (normal vs. high), site of disease (peripheral vs. deep), prior lines of treatment (1 vs. 2-3), prior consolidation (none vs. WBRT and/or ASCT), type of failure (relapsed vs. refractory disease).

Duration of response, PFS, OS, and tolerability were the secondary endpoints. Duration of response was defined as the time from the first assessment that documents the response to the date of relapse, date of death from any cause or date of the last visit of follow-up. PFS was defined as the interval between the time of entry onto trial and failure (relapsing or progressive disease), death from any cause or date of the last visit of follow-up. OS was defined as the time from entry onto trial until death from any cause or date of the last visit of follow-up. Tolerability was defined by of grade 3-4 AEs according to NCI CTCAE[19].

BBB Permeability Assessed by Neuroimaging

Variations induced by NGR-hTNF in the BBB permeability at the level of the lymphomatous lesions, areas surrounding the tumor (perilesional area) and in the normal-appearing brain parenchyma were assessed by DCE-MRI. DCE acquisition followed a standard protocol[28] that included also conventional T1, T2, Flair, DWI and Dynamic Susceptibility Contrast Perfusion (DSC) sequences. As represented in FIG. 5, DCE-MRI was performed within the conventional MRI study in day 0 (before treatment—baseline data) and day 1 (after treatment) of the 1st (R-CHOP alone), 2nd (first course of R-CHOP preceded by NGR-hTNF) and 6th (last course of R-CHOP preceded by NGR-hTNF) treatment courses. In cases of multiple lesions, the largest one was considered. Post-processing of DCE-MRI was performed using Olea software (La Ciotat, France); all dynamic images were corrected for motion artifacts and co-registered to a volumetric post-contrast T1 sequences. Results were expressed as Ktrans values normalized using contralateral white matter. Ktrans obtained after the 2nd course (measured after NGR-hTNF infusion) were compared with those obtained after the 1st course (without NGR-hTNF) to establish the effect of TNF on BBB permeabilization. Statistically significance was assessed by Wilcoxon matched pairs test.

BBB Permeability Assessed by SPECT

Changes in BBB permeability induced by NGR-hTNF were assessed also by brain scintigraphy. Because of its hydrophilic property, $^{99m}$Tc-diethylene-triamine-pentacetic acid ($^{99m}$Tc-DTPA) penetrates only the disrupted BBB, spreads into the altered tissues and binds by a not yet well elucidated mechanism. The amount of tracer's uptake at the level of the brain lesions increases proportionally to the degree of BBB permeabilization. Brain scintigraphy was acquired twice (FIG. 2), in basal condition (bBS) some days before the 3$^{rd}$ course of treatment (median 4 days, range 1-6), and after the end of the 3$^{rd}$ course (paBS). Approximately 555-740 MBq of $^{99m}$Tc-DTPA were injected as an intravenous bolus. Ninety-120 minutes later, using a dual-head γ-camera equipped by a pair of low-energy, high-resolution collimators, a SPECT/CT study was performed. Both for bBS and paBS, qualitative and semi-quantitative evaluations were performed. In particular, for semi-quantitative evaluation, PMOD software (ver. 3.2, PMOD Technologies, Swiss) was used, assessing the volume of $^{99m}$Tc-DTPA uptake. A volume of interest of 30% of maximum uptake was drawn around the $^{99m}$Tc-DTPA positive area(s) by an automatic isocontour method. Statistically significance of changes in volume of $^{99m}$Tc-DTPA uptake between bBS and paBS was assessed by Wilcoxon matched pairs test.

Expression of the Target Receptor of the CNGRCG Peptide (CD13)

The CNGRCG moiety of NGR-hTNF can recognize a CD13 form expressed by tumor vessels, resulting in targeted delivery of TNF to the tumor endothelium. The presence of this CD13 form in treated tumors was assessed by immunohistochemical and immunofluorescence techniques on paraffin-embedded specimens of diagnostic tissue samples of enrolled patients. CD13 expression did not condition patient registration in the trial or experimental treatment.

Immunohistochemical analysis was performed automatically using the immunostainer Ventana-Roche Ultrabenchmark XT, the anti-CD13 monoclonal antibody (mAb) SP187, and the anti-α-smooth muscle actin (αSMA—a marker of pericytes) mAb 1A4 (Sigma, 10 µg/ml). Immunofluorescence staining was performed, after antigen retrieval, using an anti-CD13 polyclonal antibody (1051-RP02, SinoBiological, 1:500) and the anti-αSMA antibody (mAb 1A4, Sigma, 10 µg/ml) in 1% BSA, 5% normal horse serum, 0.1% Triton X-100 in PBS. After o.n. incubation, antibody binding was detected using a mixture of secondary antibodies consisting of donkey anti-rabbit IgG-Alexa Fluor 488 (green) (4 µg/ml) and donkey anti-mouse IgG-Alexa Fluor 647 (infrared) (4 µg/ml) conjugates. Nuclear staining was performed with DAPI (blue). Fluorescence signals were acquired using an inverted point scanning confocal SMD-SP8 Leica Microsystem equipped with 40×/0.4 objective lens, a Navigator Module and the LASX acquisition software.

Results

Assessable Study Population

Twenty-eight patients were registered between May 2016 and December 2018. All patients were assessable for activity and tolerability. Median age of the 28 assessed patients was 58 years old (range 26-78); 14 were males (Table 3).

TABLE 3

| Patient characteristics (n = 28) | |
| --- | --- |
| Median Age | 58 (range 26-78) |
| Male:Female | 1 |
| ECOG - Performance Status >1 | 15 (53%) |
| High lactic dehydrogenase serum level | 11 (40%) |
| High cerebrospinal-fluid protein concentration* | 11/22 (50%) |
| Involvement of deep areas | 12 (43%) |
| IELSG risk score | |
| Low | 5 (18%) |
| Intermediate | 19 (68%) |
| High | 4 (14%) |
| Intraocular disease | 3 (10%) |
| Meningeal dissemination | 0 (0%) |
| Prior lines | |
| Prior lines ≥2 | 10 (36%) |
| Prior Autologous Stem Cell transplantation (ASCT) | 7 (25%) |
| Prior Whole-Brain Irradiation (WBRT) | 6 (21%) |
| Both ASCT + WBRT | 4 (14%) |
| Refractory to prior lines | 15 (54%) |

*Lumbar puncture was contraindicated in six patients; CSF protein concentration was considered as unfavorable feature in IELSG risk score in these patients.

Most patients had unfavorable features at trial registration: 23 (82%) patients had intermediate-high IELSG risk score, with an ECOG-PS≥2 in 15 patients, increased LDH serum level in 11, high CSF protein concentration in 11, involvement of deep areas of the brain in 12. All patients displayed brain parenchymal lesions, with concomitant intraocular disease in three; no patient had meningeal disease. Patients were heavily pretreated; ten received two or more prior treatment lines; 17 (61%) patients had received ASCT, WBRT or both. Lymphoma was refractory to prior therapies in 15 (54%) patients.

Toxicity

Experimental treatment was well tolerated (Table 4).

TABLE 4

| Toxicity per course of treatment | | | | |
| --- | --- | --- | --- | --- |
| | Grade 1-2 | Grade 3 | Grade 4 | Grade 5 |
| Neutropenia | 9 (7%) | 17 (13%) | 57 (43%) | — |
| Thrombocytopenia | 34 (26%) | 25 (19%) | 26 (20%) | — |
| Anemia | 86 (65%) | 12 (9%) | 2 (2%) | — |
| Febrile Neutropenia | — | 5 (4%) | 1 (1%) | — |
| Hepatotoxicity | 27 (20%) | 4 (3%) | 1 (1%) | — |
| Oral Mucositis | 1 (1%) | 3 (2%) | — | — |
| Infections | — | 5 (4%) | — | — |
| Seizures | 3 (2%) | — | — | — |
| Deep Vein Thrombosis | 2 (2%) | — | — | — |
| Syncope | — | 2 (2%) | — | — |
| LVEF reduction | 1 (1%) | — | — | — |
| Constipation | 2 (2%) | 1 (1%) | — | — |
| Nausea and vomiting | 4 (3%) | — | — | — |
| TNF Infusion reaction* | 9 (7%) | — | — | — |

All toxic events other than alopecia are reported. Denominator is the total number of delivered courses (n = 132). LVEF = left ventricular ejection function.
*Fever (n = 4), chills (4), arterial hypertension (1).

132 (79%) of the 168 planned courses were delivered. There were no cases of unexpected toxicity or interruptions due to toxicity and no patient required dose reductions. Treatment delay was recorded only in six (4%) courses due to cytopenia. Sixteen severe adverse events were recorded in 12 patients: seizures (3), deep venous thrombosis (2), grade-3 infections (5), grade-3 syncope (2), grade-3 constipation, grade-4 febrile neutropenia, pulmonary aspergillosis, and grade-2 left ventricular function reduction. There were nine cases of reaction to NGR-hTNF infusion; all of them, fever (4), chills (4) and arterial hypertension, were of grade 1-2 and were solved after infusion interruption for 15 minutes and symptomatic medication. As per-protocol, infusion was delayed and completed one hour later. These patients received other courses of NGR-hTNF/R-CHOP with per-protocol prophylaxis without experiencing any further infusion reaction. Twelve patients required blood/platelets transfusions (seven of them had received prior ASCT).

Activity (Primary Endpoint)

The best response to NGR-hTNF/R-CHOP combination was complete in 11 patients (examples in FIG. 7) and partial in ten, with an ORR of 75% (95% CI=59-91%); seven patients experienced PD. The predetermined activity threshold of at least 12 responses was largely achieved. The best response was achieved after the second course in 14 patients and after the fourth course in seven. Responses were equally distributed in analyzed subgroups according to IELSG risk variables, site and number of lesions, prior therapies, and refractoriness (Table 5).

TABLE 5

Associations between responses and clinical and therapeutic variables

| Variables | Analyzed subgroups | Number of pts | Objective response | P value[1] |
|---|---|---|---|---|
| Age | ≤60 years | 16 | 11 (69%) | |
| | >60 years | 12 | 10 (83%) | 0.33 |
| ECOG performance status | 1 | 13 | 10 (77%) | |
| | 2-3 | 15 | 11 (73%) | 1.00 |
| LDH serum level | normal | 17 | 12 (71%) | |
| | high | 11 | 9 (81%) | 0.67 |
| CSF protein level | normal | 11 | 9 (81%) | |
| | high | 11 | 8 (73%) | 1.00 |
| Site of disease | peripheral | 16 | 13 (81%) | |
| | deep | 12 | 8 (67%) | 0.42 |
| Prior treatment lines | 1 | 18 | 12 (67%) | |
| | 2-3 | 10 | 9 (90%) | 0.36 |
| Prior consolidation | none | 11 | 7 (64%) | |
| | WBRT or ASCT | 17 | 14 (82%) | 0.38 |
| Type of failure | relapsed disease | 13 | 11 (85%) | |
| | refractory disease | 15 | 10 (67%) | 0.39 |

[1]Fisher exact test.

Seventeen of the 21 responding patients received consolidation: WBRT in seven patients, ASCT in five, lenalidomide maintenance in one, and combinations of these therapies in four. Two of the three patients with intraocular disease achieved a tumor regression at that site and did not experienced intravitreal relapse at 3 and 28 months of follow-up. Response lasted more than 6 months in all complete responders (median 10 months; range 6-19). At a median follow-up of 16 months (range 9-26), five patients remain relapse-free and six patients are alive.

NGR-hTNF Inhibitors (Biomarker Assessment)

A near-significant association (p=0.066) was observed between plasma levels of CgA at trial registration and CR rate (FIG. 8A). When patients were grouped in those with "low" and "high" CgA levels, using a ROC-driven cut-off of 1.4 nM, we observed 8/13 and 3/15 patients, respectively, achieving a CR (62% vs. 20%; p=0.05). Notably, plasma levels of CgA at trial registration were associated with the assumption of PPIs during prior steroid therapy. Median plasma levels of CgA were 1.05 nM (range 0.29-3.27) and 2.26 nM (range 0.33-7.99; p=0.008) respectively in patients who did not take PPIs (n=14) and PPI-treated patients (n=14). CgA concentrations were progressively reduced in some patients after PPI interruption (FIG. 8B), while the values remained stable in patients who had not received this drug (FIG. 8C).

Median plasma levels of sTNF-R1 and sTNF-R2 at trial registration were 0.66 (range 0.32-4.88) and 2.14 (range 0.98-7.26) nM, respectively. sTNF-Rs concentrations were not associated with response to NGR-hTNF/R-CHOP, did not change after PPI interruption and remained stable during treatment (data not shown).

Expression of CD13 in PCNSL Vasculature

Immunohistochemical staining demonstrated the presence of CD13 in diagnostic brain biopsies of enrolled patients; stained vessels in most instances showed narrowed lumina with irregular outlines. An example of CD13-positive vascular signal within lymphomatous lesion is shown in FIG. 6A. Immunohistochemical and confocal immunofluorescence analysis of tissue sections stained with an anti-CD13 polyclonal antibody and with anti-αSMA (a marker of pericytes) antibody showed that most stained vessels lacked pericyte layer (FIG. 6B), pointing to immature vessels. 3D projections of more mature vessels showed that CD13 was expressed by the endothelial lining of vessels, while it was much less expressed or almost absent in pericytes (FIG. 6C-D). These findings point toward the fact that CD13 is expressed in the endothelial luminal side of the tumor vasculature, which is accessible to NGR-hTNF delivered by intravenous route.

Double staining experiments with anti-CD13 (NGR target) and anti-PDGFR-β (pericyte marker) antibodies revealed a broad expression of CD13 in pericytes of almost all lymphoma-associated vessels (FIG. 10). Furthermore, double staining experiments with anti-CD13 and anti-CD31 (endothelial marker) antibodies revealed CD13 expression also in the endothelial lining of tumor vessels (FIG. 9A-C). Tumor vessels with CD13-positive pericytes cells and CD13-negative endothelial cells were also observed (FIG. 9D).

BBB Permeability Assessed by Neuroimaging

DCE-MRI analysis showed that vascular permeability was increased after NGR-hTNF infusion (FIG. 4). This effect was more evident in perilesional areas. The median (range) Ktrans of contrast-enhanced areas after the first course of R-CHOP (without NGR-hTNF) was 23.5 (6.8-98.8) and raised to 35.3 (23.9-887.7; p=0.39) after the second course (NGR-hTNF/R-CHOP combination). In perilesional areas, baseline values (R-CHOP alone) were lower (median 2.5; range 0.4-3.9), but significantly raised to 4.7 (2.2-37.7; p=0.01) after NGR-hTNF infusion in the second course (NGR-hTNF/R-CHOP combination).

BBB Permeability Assessed by SPECT

The capability of NGR-hTNF to increase the BBB permeability in tumor and perilesional areas was confirmed by SPECT studies. Quantitative analysis showed an increase in the extent of the $^{99m}$Tc-DTPA positive region(s) in all the investigated cases (an example in FIG. 5). The median volume of ≥30% $^{99m}$Tc-DTPA uptake (volume of interest) measured by PMOD before and after the infusion of NGR-hTNF and R-CHOP was 26 cm$^3$ (range 5-67) and 40 cm$^3$ (range 10-92), respectively (p=0.028). There was a median volume increase of 45%, with a range of 14%-87%.

DISCUSSION

The herein presented results of the INGRID phase II trial demonstrate that NGR-hTNF/R-CHOP combination is well tolerated and highly active in heavily pretreated patients with relapsed/refractory PCNSL. Importantly, most of treated patients were referred to consolidation therapy following tumor regression after NGR-hTNF/R-CHOP, which increase the probabilities of cure in these poor-prognosis patients. Activity of this innovative strategy is in line with selective enhancement of vascular permeability in the tumor and peritumoral areas. The specificity of NGR-hTNF effects is supported also by the lack of changes in concentrations of R-CHOP drugs in plasma and CSF samples, demonstrated in the exploratory phase of the trial[14], and by the high level of expression of CD13, the target of NGR-hTNF, in endothelial cells and pericytes of tumor-associated capillaries, as demonstrated in the present study. Taken together, the results of this trial support that increasing the BBB permeability and drug penetration in the tumor by non-invasive procedures is an attractive therapeutic approach in PCNSL patients.

Experience in PCNSL patients with CHOP in the pre-rituximab era and, more recently, with R-CHOP actually demonstrates that this combination is ineffective in PCNSL patients, both at presentation and relapse[5,24-26], and confirm the common belief that this inefficacy is mostly due to the poor CNS bioavailability of related drugs. Indeed, when used as upfront treatment, CHOP chemotherapy was associated with low response rate and did not contribute to improve disease control in combination with high-dose-methotrexate-based chemotherapy or with WBRT, with a 2-year overall survival after CHOP-WBRT of only 20-40%[5,24-26]. Studies focused on CHOP with or without rituximab in patients with relapsed or refractory PCNSL are not available; however, the disappointing results reported as first-line treatment[5,24-26] suggest that CHOP with or without rituximab should be inactive also as salvage therapy. This view is also supported by the lack of significant responses after the first cycle of R-CHOP alone in the first 10 enrolled patients[14], at a variance with the ORR of 75% and the possibility to deliver a consolidation therapy in 17 of the 21 patients responding to the NGR-hTNF/R-CHOP combination therapy. The activity results obtained with NGR-hTNF/R-CHOP were associated with an excellent safety profile, without unexpected toxicities and, importantly, with a maintained dose intensity in all cases. In line with prior trials[27-29], the addition of low doses of NGR-hTNF to chemotherapeutic agents was associated with good tolerability, and, in particular, the association with doxorubicin was not associated with severe cardiovascular events.

Previous studies focused on NGR-hTNF and its synergistic effects with chemotherapeutic agents, both in animal models and patients with solid tumors, have shown that the selectivity of NGR-hTNF for tumor vessels requires the interaction with specific receptors[11,12,30]. When delivered at low doses, NGR-hTNF engages high-avidity interactions with CD13, TNF-R1 and TNF-R2 on endothelial cells that express these receptors, as in the angiogenic tumor vasculature[7], but not with endothelial cells that do not express CD13, as it occurs in non-neoplastic tissues. Indeed, a peculiar form of CD13 is expressed by the angiogenic vessels of tumors and of other tissues, but not (or barely) by blood vessels of normal tissues[8,32]. Remarkably, NGR-containing drugs can selectively target the CD13 form expressed by endothelial cells and pericytes in tumor blood vessels, but not the CD13 forms expressed by other tissues[10,32]. In the exploratory phase of this trial[14], we have shown that the pro-permeabilizing effect of NGR-hTNF is more evident in tumor and peritumoral areas, where expression of CD13 by the tumor vessels was demonstrated by immunohistochemistry and immunofluorescence techniques. Of note, CD13 was found to be abundantly expressed by pericytes and, to a lower extent, by endothelial cells of PCNSL vasculature. Importantly, these cells, especially in the latter case, are highly accessible to intravenously delivered NGR-hTNF. Notably, previous studies regarding the expression of CD13 in normal brain have shown that pericytes, but not endothelial cells, express this marker[33,34]. The capability of NGR-hTNF to recognize the CD13 form expressed by pericytes in the normal brain remains to be elucidated, but the following observations suggest that only tumor blood vessels, are targeted in PCNSL patients: first, enhanced uptake of $^{99m}$Tc-DTPA in tumoral/peritumoral areas, but not in residual normal brain, has been observed by SPECT after NGR-hTNF therapy[14]; second, no changes in the concentration of R-CHOP drugs in plasma and CSF occurred in patients after NGR-hTNF treatment[14]. One possible explanation for the selective drug penetration is that NGR-hTNF, by targeting $CD13^+$ endothelial cells in the tumor vasculature, further increases their permeability, thereby promoting selective local drug penetration. It is also possible that TNF receptors are overexpressed in tumor vessels compared to normal vessels, as previously observed for brain metastases[6], thereby leading to multivalent high avidity interaction of low-dose NGR-hTNF with CD13 and TNF receptors in tumors vessels, but not in normal brain vessels.

In the present study, plasma levels of sTNF-Rs were not related to therapeutic outcome, whereas significant associations were observed among plasma levels of CgA, use of PPIs, and response to NGR-hTNF/R-CHOP. Plasma levels of CgA are known to increase after treatment with PPIs, since these drugs induce hypergastrinemia and stimulation of enterochromaffin cells to secrete CgA[36-38]. Accordingly, inventors observed that administration of PPIs to PCNSL patients, performed to prevent gastric toxicity during steroid therapy and chemotherapy, led to a significant increase of circulating CgA. Using a ROC-driven cut-off, they also observed that 62% of patients with low CgA plasma levels and 27% of patients with high CgA levels achieved a CR to NGR-hTNF/R-CHOP (p=0.066). This finding supports that discontinuation of PPIs before NGR-hTNF/R-CHOP therapy is advisable. When possible, NGR-hTNF/R-CHOP should be started once CgA reaches normal levels after PPI discontinuation, which may requires from few days to some weeks[36-38].

In conclusion, the results of the INGRID trial support that pro-permeabilizing effects of low-dose NGR-hTNF on the BBB can be exploited to enhance the activity of R-CHOP in PCNSL. The NGR-hTNF/R-CHOP combination therapy is active and safe in heavily pretreated patients with relapsed/refractory PCNSL, and its antitumor activity is in line with expression of CD13 in tumor vessels. PPIs should be avoided before and during this therapy because they can mitigate the effects of NGR-hTNF by enhancing the plasma levels of CgA. This innovative approach deserves to be addressed as first-line treatment in PCNSL patients.

REFERENCES

1. Batchelor T T. Primary central nervous system lymphoma. Hematology Am Soc Hematol Educ Program 2016; 2016: 379-85.
2. Ferreri A J M, Holdhoff M, Nayak L, Rubenstein J L. Evolving Treatments for Primary Central Nervous System Lymphoma. Am Soc Clin Oncol Educ Book 2019; 39:454-66.
3. Ferreri A J, Cwynarski K, Pulczynski E, et al. Chemoimmunotherapy with methotrexate, cytarabine, thiotepa, and rituximab (MATRix regimen) in patients with primary CNS lymphoma: results of the first randomisation of the International Extranodal Lymphoma Study Group-32 (IELSG32) phase 2 trial. Lancet Haematol 2016; 3: e217-27.
4. Ferreri A J M. Therapy of primary CNS lymphoma: role of intensity, radiation, and novel agents. Hematology Am Soc Hematol Educ Program 2017; 2017:565-77.
5. Mead G M, Bleehen N M, Gregor A, et al. A medical research council randomized trial in patients with primary cerebral non-Hodgkin lymphoma: cerebral radiotherapy with and without cyclophosphamide, doxorubicin, vincristine, and prednisone chemotherapy. Cancer 2000; 89:1359-70.
6. Connell J J, Chatain G, Cornelissen B, et al. Selective permeabilization of the blood-brain barrier at sites of metastasis. J Natl Cancer Inst 2013; 105:1634-43.
7. Corti A, Curnis F, Rossoni G, Marcucci F, Gregorc V. Peptide-mediated targeting of cytokines to tumor vasculature: the NGR-hTNF example. BioDrugs 2013; 27:591-603.

8. Di Matteo P, Arrigoni G L, Alberici L, et al. Enhanced expression of CD13 in vessels of inflammatory and neoplastic tissues. J Histochem Cytochem 2011; 59:47-59.
9. Curnis F, Sacchi A, Borgna L, Magni F, Gasparri A, Corti A. Enhancement of tumor necrosis factor alpha antitumor immunotherapeutic properties by targeted delivery to aminopeptidase N (CD13). Nat Biotechnol 2000; 18:1185-90.
10. Curnis F, Arrigoni G, Sacchi A, et al. Differential binding of drugs containing the NGR motif to CD13 isoforms in tumor vessels, epithelia, and myeloid cells. Cancer Res 2002; 62:867-74.
11. Curnis F, Sacchi A, Corti A. Improving chemotherapeutic drug penetration in tumors by vascular targeting and barrier alteration. J Clin Invest 2002; 110:475-82.
12. Sacchi A, Gasparri A, Gallo-Stampino C, Toma S, Curnis F, Corti A. Synergistic antitumor activity of cisplatin, paclitaxel, and gemcitabine with tumor vasculature-targeted tumor necrosis factor-alpha. Clin Cancer Res 2006; 12:175-82.
13. Gregorc V, Gaafar R M, Favaretto A, et al. NGR-hTNF in combination with best investigator choice in previously treated malignant pleural mesothelioma (NGR015): a randomised, double-blind, placebo-controlled phase 3 trial. Lancet Oncol 2018; 19:799-811.
14. Ferreri A J M, Calimeri T, Conte G M, et al. R-CHOP preceded by blood-brain barrier permeabilization with engineered tumor necrosis factor-alpha in primary CNS lymphoma. Blood 2019; 134:252-62.
15. Dondossola E, Gasparri A M, Colombo B, Sacchi A, Curnis F, Corti A. Chromogranin A restricts drug penetration and limits the ability of NGR-TNF to enhance chemotherapeutic efficacy. Cancer Res 2011; 71:5881-90.
16. Gut P, Waligorska-Stachura J, Czarnywojtek A, et al. Management of the hormonal syndrome of neuroendocrine tumors. Arch Med Sci 2017; 13:515-24.
17. Swerdlow S H, Campo E, Harris N L, Pileri S, et al. WHO classification of tumors of Haematopoietic and Lymphoid Tissues. Lyon, France: IARC Press ed., 2008.
18. Ferreri A J, Blay J Y, Reni M, et al. Prognostic scoring system for primary CNS lymphomas: the International Extranodal Lymphoma Study Group experience. J Clin Oncol 2003; 21:266-72.
19. Trotti A, Colevas A D, Setser A, et al. CTCAE v3.0: development of a comprehensive grading system for the adverse effects of cancer treatment. Semin Radiat Oncol 2003; 13:176-81.
20. Abrey L E, Batchelor T T, Ferreri A J, et al. Report of an international workshop to standardize baseline evaluation and response criteria for primary CNS lymphoma. J Clin Oncol 2005; 23:5034-43.
21. Crippa L, Bianco M, Colombo B, et al. A new chromogranin A-dependent angiogenic switch activated by thrombin. Blood 2013; 121:392-402.
22. Reni M, Zaja F, Mason W, et al. Temozolomide as salvage treatment in primary brain lymphomas. Br J Cancer 2007; 96:864-7.
23. Mappa S, Marturano E, Licata G, et al. Salvage chemo-immunotherapy with rituximab, ifosfamide and etoposide (R-IE regimen) in patients with primary CNS lymphoma relapsed or refractory to high-dose methotrexate-based chemotherapy. Hematol Oncol 2012.
24. O'Neill B P, Wang C H, O'Fallon J R, et al. Primary central nervous system non-Hodgkin's lymphoma (PCNSL): survival advantages with combined initial therapy? A final report of the North Central Cancer Treatment Group (NCCTG) Study 86-72-52. Int J Radiat Oncol Biol Phys 1999; 43:559-63.
25. Laack N N, O'Neill B P, Ballman K V, et al. CHOD/BVAM chemotherapy and whole-brain radiotherapy for newly diagnosed primary central nervous system lymphoma. Int J Radiat Oncol Biol Phys 2011; 81:476-82.
26. Schultz C, Scott C, Sherman W, et al. Preirradiation chemotherapy with cyclophosphamide, doxorubicin, vincristine, and dexamethasone for primary CNS lymphomas: initial report of radiation therapy oncology group protocol 88-06. J Clin Oncol 1996; 14:556-64.
27. van Laarhoven H W, Fiedler W, Desar I M, et al. Phase I clinical and magnetic resonance imaging study of the vascular agent NGR-hTNF in patients with advanced cancers (European Organization for Research and Treatment of Cancer Study 16041). Clin Cancer Res 2010; 16:1315-23.
28. Gregorc V, Citterio G, Vitali G, et al. Defining the optimal biological dose of NGR-hTNF, a selective vascular targeting agent, in advanced solid tumours. Eur J Cancer 2010; 46:198-206.
29. Gregorc V, Santoro A, Bennicelli E, et al. Phase Ib study of NGR-hTNF, a selective vascular targeting agent, administered at low doses in combination with doxorubicin to patients with advanced solid tumours. Br J Cancer 2009; 101:219-24.
30. Calcinotto A, Grioni M, Jachetti E, et al. Targeting TNF-alpha to neoangiogenic vessels enhances lymphocyte infiltration in tumors and increases the therapeutic potential of immunotherapy. J Immunol 2012; 188:2687-94.
31. Tartaglia L A, Pennica D, Goeddel D V. Ligand passing: the 75-kDa tumor necrosis factor (TNF) receptor recruits TNF for signaling by the 55-kDa TNF receptor. J Biol Chem 1993; 268:18542-8.
32. Pasqualini R, Koivunen E, Kain R, et al. Aminopeptidase N is a receptor for tumor-homing peptides and a target for inhibiting angiogenesis. Cancer Res 2000; 60:722-7.
33. Kunz J, Krause D, Kremer M, Dermietzel R. The 140-kDa protein of blood-brain barrier-associated pericytes is identical to aminopeptidase N. J Neurochem 1994; 62:2375-86.
34. Alliot F, Rutin J, Leenen P J, Pessac B. Pericytes and periendothelial cells of brain parenchyma vessels co-express aminopeptidase N, aminopeptidase A, and nestin. J Neurosci Res 1999; 58:367-78.
35. Desar I M, van Herpen C M, van Asten J J, et al. Factors affecting the unexpected failure of DCE-MRI to determine the optimal biological dose of the vascular targeting agent NGR-hTNF in solid cancer patients. Eur J Radiol 2011; 80:655-61.
36. Korse C M, Muller M, Taal B G. Discontinuation of proton pump inhibitors during assessment of chromogranin A levels in patients with neuroendocrine tumours. Br J Cancer 2011; 105:1173-5.
37. Pregun I, Herszenyi L, Juhasz M, et al. Effect of proton-pump inhibitor therapy on serum chromogranin a level. Digestion 2011; 84:22-8.
38. Mosli H H, Dennis A, Kocha W, Asher L J, Van Uum S H. Effect of short-term proton pump inhibitor treatment and its discontinuation on chromogranin A in healthy subjects. J Clin Endocrinol Metab 2012; 97: E1731-5.

The invention claimed is:

1. A method for the treatment of primary central nervous system lymphoma in a subject, comprising administering a combination of R-CHOP (rituximab, cyclophosphamide, doxorubicin, vincristine and prednisone) and NGR-hTNF or an analog thereof:
wherein NGR-hTNF or of an analog thereof is administered after the administration of rituximab and before the administration of CHOP drugs cyclophosphamide, doxorubicin, vincristine and prednisone and wherein the analog of NGR-hTNF is selected from the group consisting of CNGRCVSGCAGRC (SEQ ID NO: 2), NGRAHA (SEQ ID NO: 3), GNGRG (SEQ ID NO: 4), cycloCVLNGRMEC (SEQ ID NO: 5) cycloCNGRC (SEQ ID NO: 6), or CNGRC (SEQ ID NO: 7).

2. The method according to claim 1 wherein the course of R-CHOP consists of 375 mg/m$^2$ of rituximab, 750 mg/m$^2$ of cyclophosphamide, 50 mg/m$^2$ of doxorubicin and 1.4 mg/m$^2$ of vincristine.

3. The method according to claim 1 wherein the NGR-hTNF administration consists of 0.8 μg/m$^2$.

4. The method according to claim 1 comprising six courses of the administration of NGR-hTNF or of an analog thereof after the administration of rituximab and before the administration of CHOP drugs cyclophosphamide, doxorubicin, vincristine and prednisone.

5. The method according to claim 1 wherein the administration of NGR-hTNF or of an analog thereof after the administration of rituximab and before the administration of CHOP drugs cyclophosphamide, doxorubicin, vincristine and prednisone is separated by 18 to 21 days.

6. The method according to claim 1 wherein primary central nervous system lymphoma is a relapsed or a refractory primary central nervous system lymphoma.

7. The method according to claim 1 wherein the analog of NGR-hTNF is CNGRC (SEQ ID NO: 7).

* * * * *